(12) United States Patent
Sharma

(10) Patent No.: US 11,419,611 B2
(45) Date of Patent: Aug. 23, 2022

(54) LEFT ATRIAL APPENDAGE CLOSURE DEVICE AND METHOD

(71) Applicant: Virender K. Sharma, Paradise Valley, AZ (US)

(72) Inventor: Virender K. Sharma, Paradise Valley, AZ (US)

(*) Notice: Subject to any disclaimer, the term of this patent is extended or adjusted under 35 U.S.C. 154(b) by 0 days.

(21) Appl. No.: 17/079,371

(22) Filed: Oct. 23, 2020

(65) Prior Publication Data

US 2021/0121183 A1   Apr. 29, 2021

Related U.S. Application Data

(60) Provisional application No. 62/925,316, filed on Oct. 24, 2019.

(51) Int. Cl.
*A61B 17/12* (2006.01)
*A61B 17/00* (2006.01)

(52) U.S. Cl.
CPC .. *A61B 17/12122* (2013.01); *A61B 17/12031* (2013.01); *A61B 2017/00867* (2013.01);
(Continued)

(58) Field of Classification Search
CPC ........ A61B 17/12122; A61B 17/12031; A61B 17/12172; A61B 17/12177; A61B 17/0057; A61B 17/12109; A61B 17/12099; A61B 17/12113; A61B 17/12027; A61B 17/12036; A61B 17/1204; A61B 17/12045; A61B 17/00234; A61B 2017/00867; A61B 2017/00876; A61B 2017/1205; A61B 2017/00632; A61B 2017/00575; A61B 2017/12054; A61B 2017/00597; A61B 2017/0061; A61B 2017/00615;
(Continued)

(56) References Cited

U.S. PATENT DOCUMENTS 6,652,556 B1 * 11/2003 VanTassel ........ A61B 17/12172
606/200
8,246,649 B2 * 8/2012 Schneider ............. A61F 2/0105
606/200

(Continued)

FOREIGN PATENT DOCUMENTS

CN    104688292 A    6/2015
WO    2021081449 A1   4/2021

OTHER PUBLICATIONS

International Search Report for PCT/US2020/057219, dated Jan. 27, 2021, 2 pages.
(Continued)

*Primary Examiner* — Kelly J Bekker
*Assistant Examiner* — Paige A Codrington

(57) ABSTRACT

A device to treat a left atrial appendage (LAA) of a patient includes a tissue ingrowth member, at least one connector, a tine, and a plurality of struts connected to the tissue ingrowth member and at least one connector. A plurality of anchors extends from the tissue ingrowth member proximate the connection point of the struts to the tissue ingrowth member. The device is configured to change shape from a compressed pre-deployment configuration to at least one expanded post-deployment configuration such that the anchors puncture and lodge into cardiac tissue, occluding an ostium of the left atrial appendage.

9 Claims, 25 Drawing Sheets

(52) U.S. Cl.
CPC ............... *A61B 2017/00876* (2013.01); *A61B 2017/1205* (2013.01)

(58) Field of Classification Search
CPC .......... A61B 2017/00579; A61B 2017/00606; A61B 2017/00619; A61F 2/0009; A61F 2/01; A61F 2/0103; A61F 2/0105
USPC ........................................................ 606/200
See application file for complete search history.

(56) References Cited

U.S. PATENT DOCUMENTS

| | | | | |
|---|---|---|---|---|
| 8,801,746 B1* | 8/2014 | Kreidler | ............ | A61B 17/1215 606/200 |
| 9,883,936 B2* | 2/2018 | Sutton | ................ | A61B 17/0057 |
| 11,154,303 B2* | 10/2021 | Miles | ................ | A61B 17/1219 |
| 2003/0212433 A1 | 11/2003 | Ambrisco | | |
| 2005/0113861 A1 | 5/2005 | Corcoran | | |
| 2005/0288704 A1* | 12/2005 | Cartier | .................. | A61F 2/0103 606/200 |
| 2006/0178695 A1* | 8/2006 | Decant, Jr. | ......... | A61B 5/02007 606/200 |
| 2007/0066993 A1* | 3/2007 | Kreidler | ................ | A61F 2/2427 606/213 |
| 2007/0225748 A1* | 9/2007 | Park | ...................... | A61F 2/0105 606/200 |
| 2012/0143238 A1* | 6/2012 | Sogard | .................. | A61F 2/0105 606/200 |
| 2013/0138138 A1* | 5/2013 | Clark | ................ | A61B 17/12177 606/200 |
| 2013/0274595 A1* | 10/2013 | Kermode | .......... | A61B 17/12022 600/424 |
| 2014/0288588 A1* | 9/2014 | Lam | ...................... | A61F 2/0105 606/200 |
| 2015/0305727 A1* | 10/2015 | Karimov | .......... | A61B 17/12136 600/16 |
| 2016/0106437 A1* | 4/2016 | van der Burg | ... | A61B 17/12122 606/200 |
| 2016/0249898 A1* | 9/2016 | Widmer | ........... | A61B 17/12031 606/213 |
| 2016/0302924 A1* | 10/2016 | Boutillette | .............. | B29C 70/74 |
| 2016/0346074 A1* | 12/2016 | Tafti | ...................... | A61F 2/0108 |
| 2017/0079790 A1* | 3/2017 | Vidlund | ................ | A61F 2/2418 |
| 2017/0172742 A1* | 6/2017 | Khairkhahan | ... | A61B 17/12172 |
| 2017/0258475 A1* | 9/2017 | Mellmann | ........ | A61B 17/12145 |
| 2019/0183512 A1* | 6/2019 | Subramaniam | .. | A61B 17/12027 |
| 2019/0357916 A1* | 11/2019 | Inouye | ............ | A61B 17/12022 |
| 2020/0205840 A1* | 7/2020 | Adawi | ............ | A61B 17/12177 |
| 2021/0137507 A1* | 5/2021 | Keren | ............. | A61B 17/12122 |
| 2021/0236102 A1* | 8/2021 | Perszyk | ........... | A61B 17/12122 |

OTHER PUBLICATIONS

Written Opinion of the International Searching Authority for PCT/US2020/057219, dated Jan. 27, 2021, 9 pages.

* cited by examiner

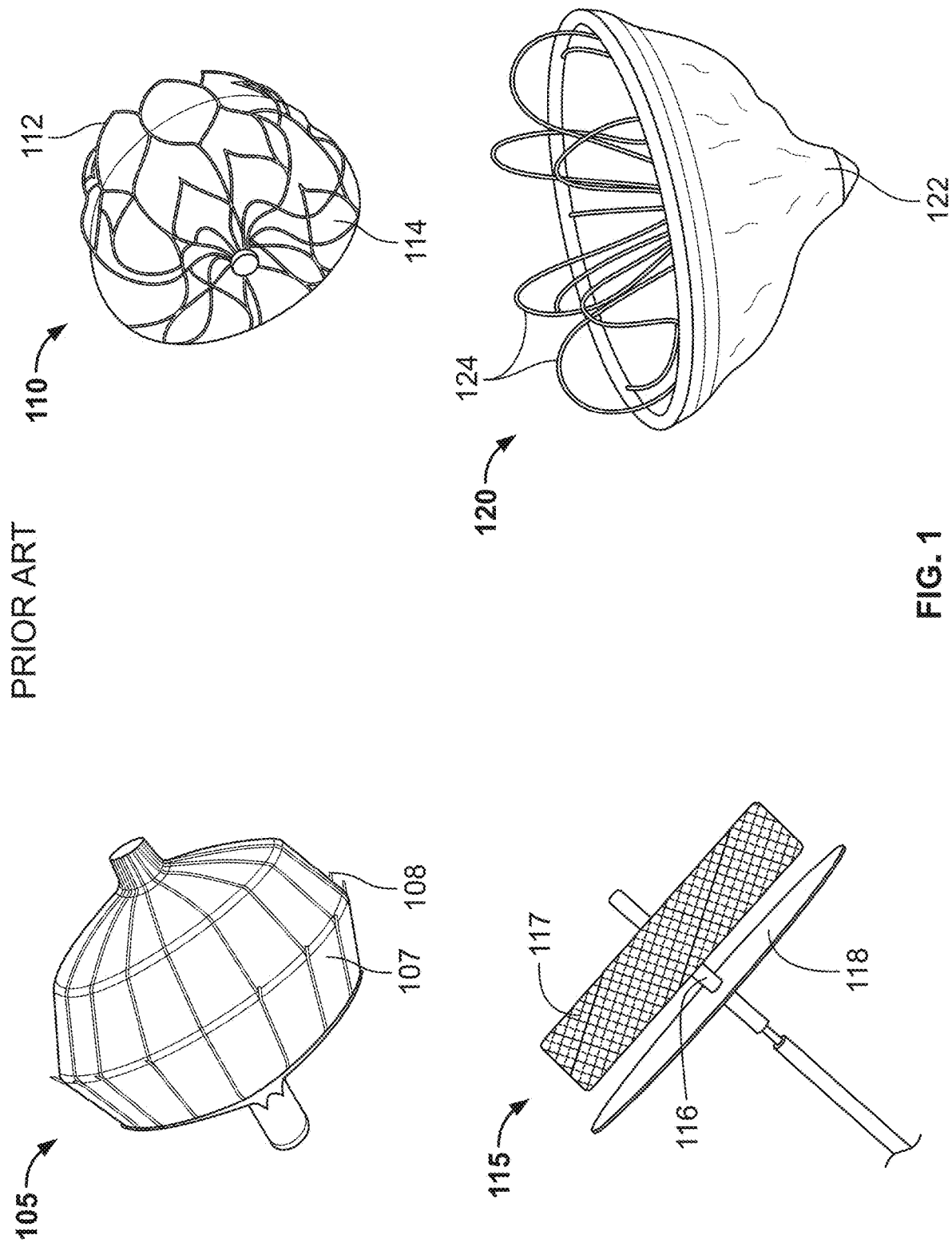

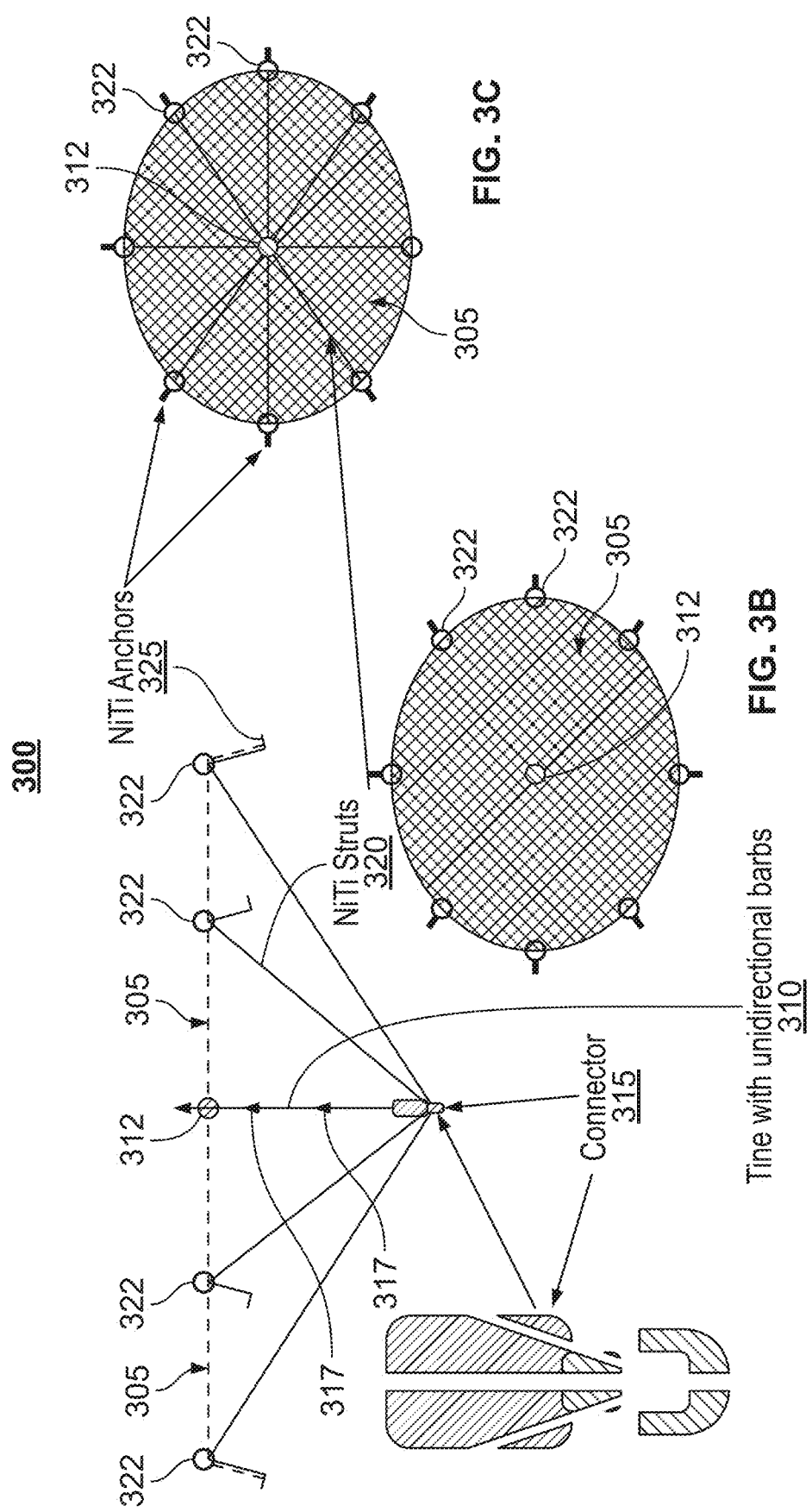

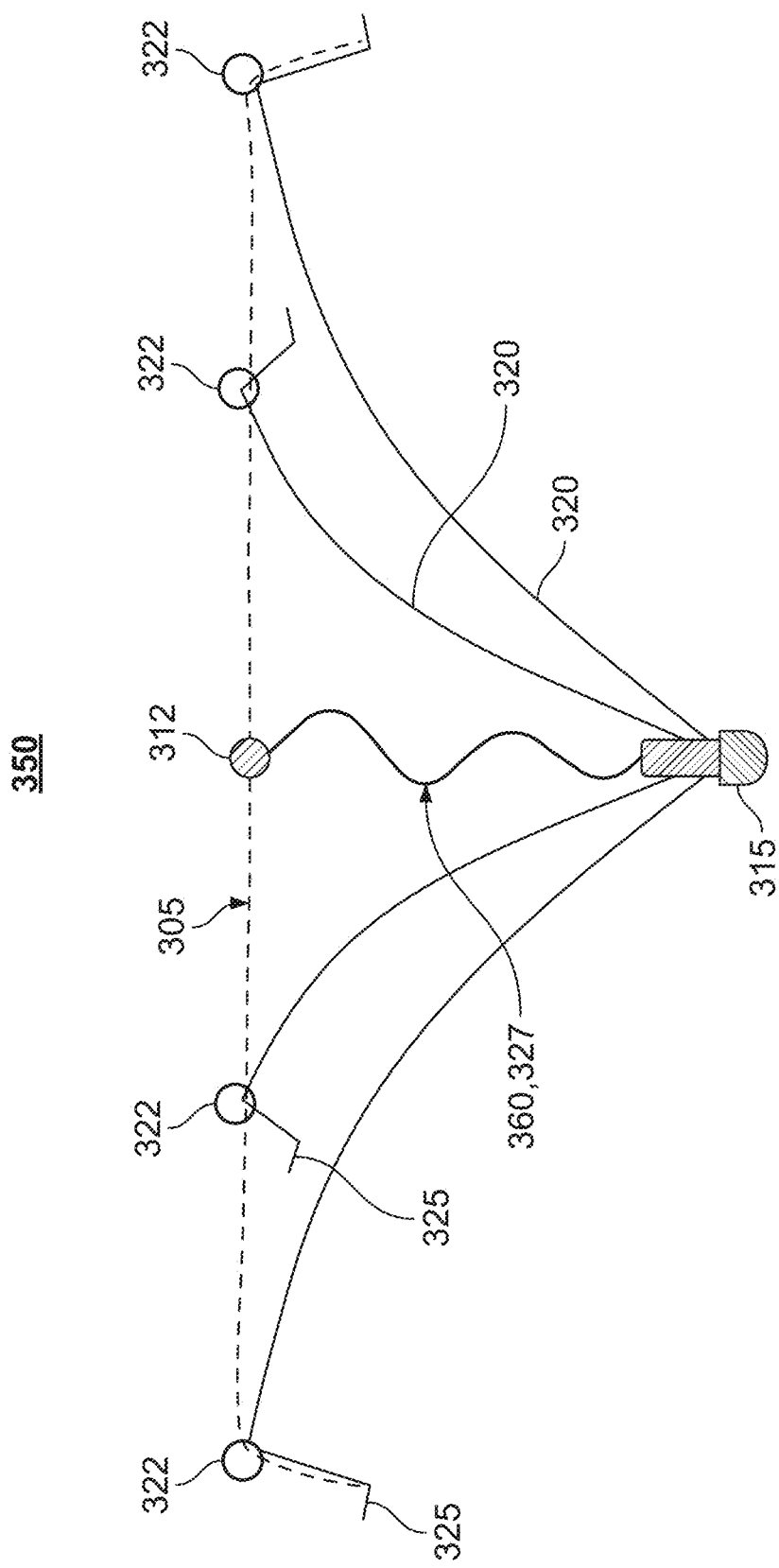

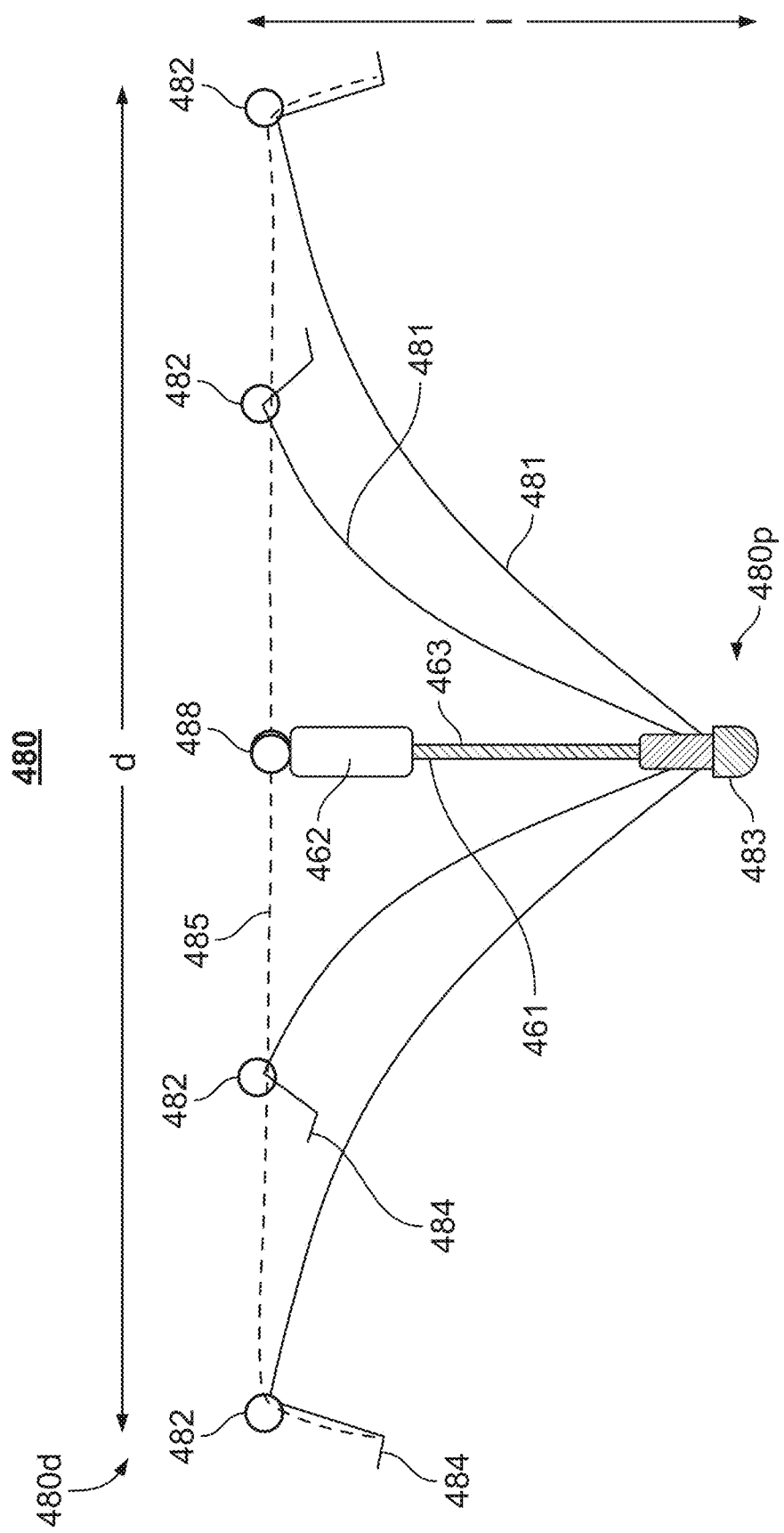

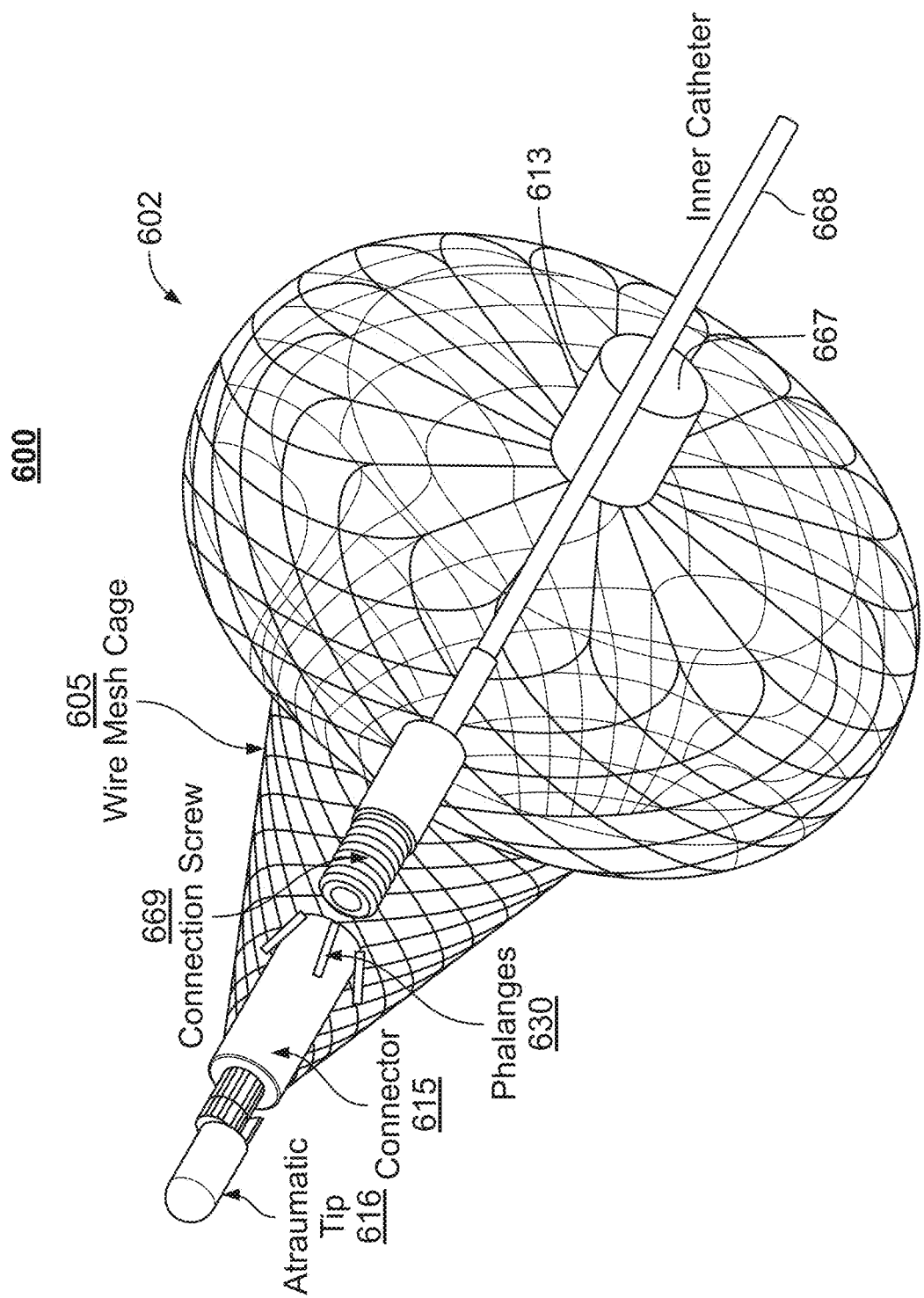

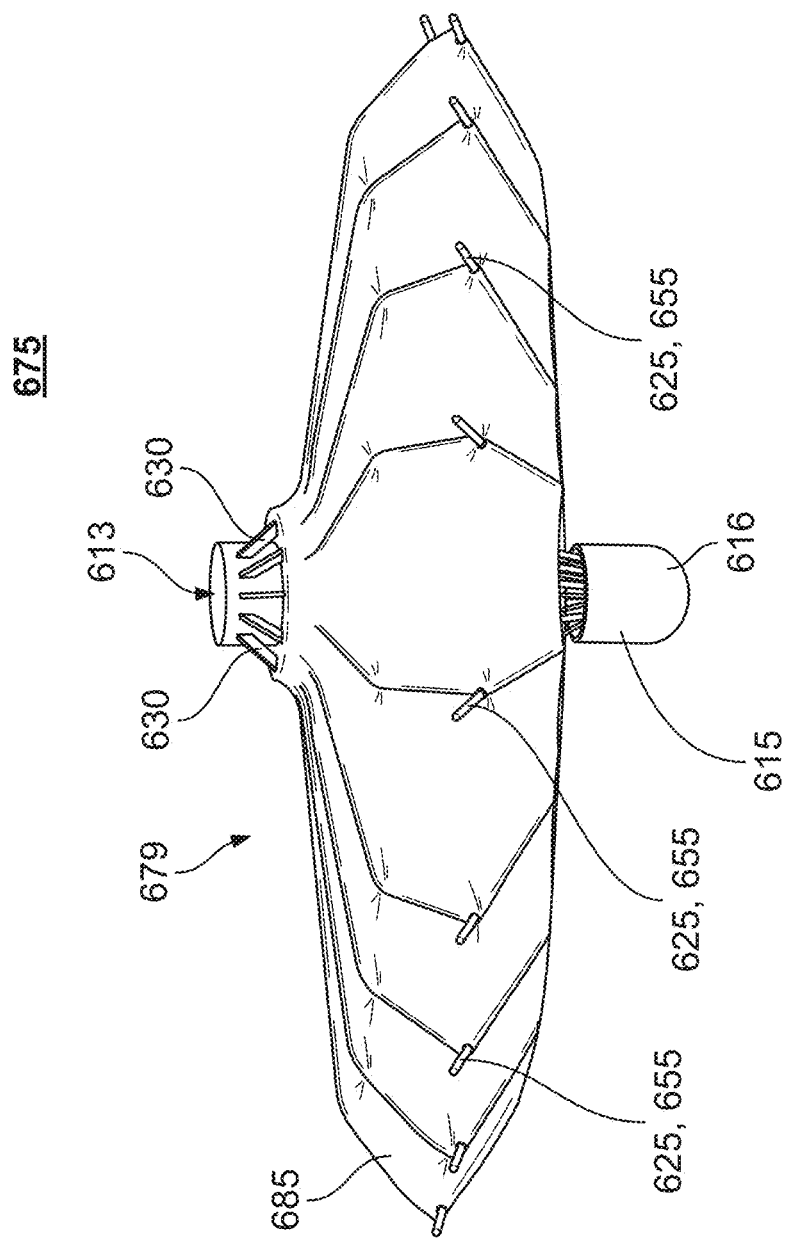

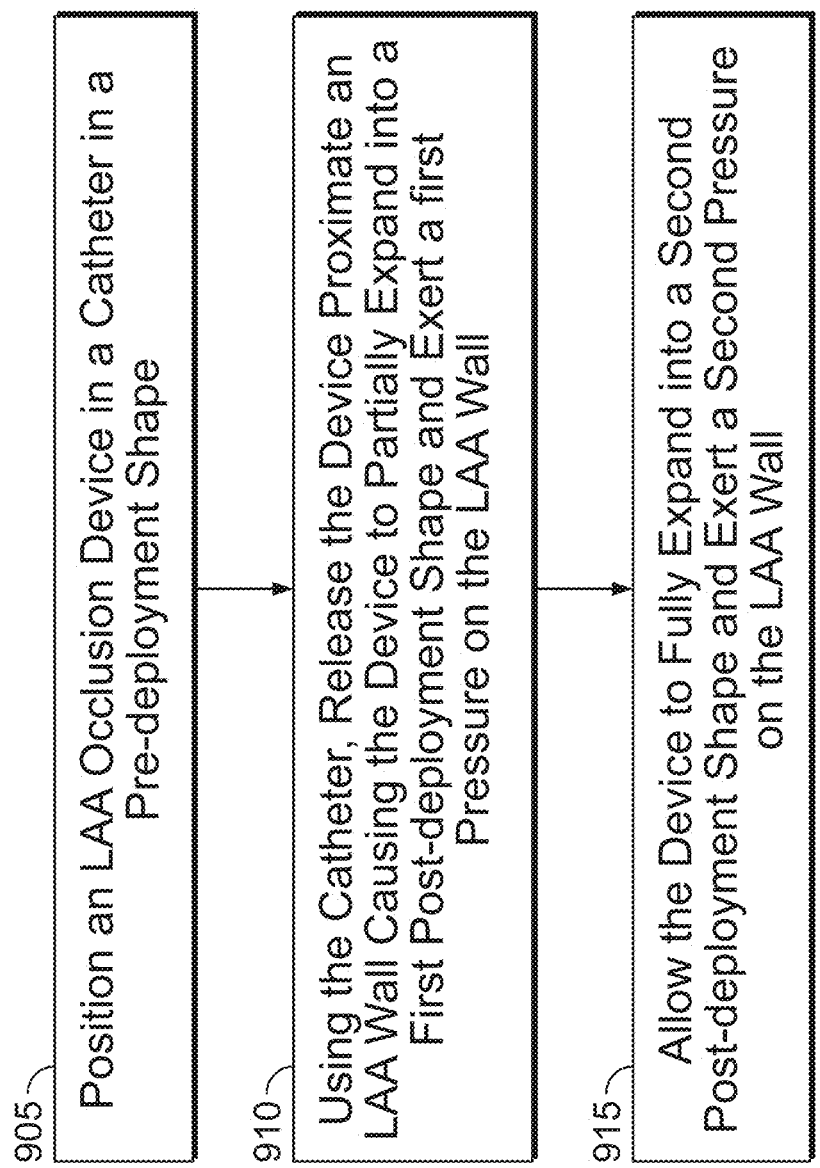

LEFT ATRIAL APPENDAGE CLOSURE DEVICE AND METHOD

CROSS-REFERENCE

The present application relies on U.S. Patent Provisional Application No. 62/925,316, entitled "Left Atrial Appendage Closure Device and Method" and filed on Oct. 24, 2019, for priority, which is herein incorporated by reference in its entirety.

FIELD

The present specification relates to systems and methods configured to close a left atrial appendage (LAA). More particularly, the present specification relates to devices having a pre-deployment shape and at least one post-deployment shape configured to exert pressure on an LAA wall to close the LAA.

BACKGROUND

A left atrial appendage (LAA), comprising a small sac in a wall of a left atrium, can be a source of both atrial arrhythmias as well as emboli which can cause strokes. Left atrial appendage occlusion and ligation devices are used to eliminate atrial arrhythmias and emboli from clots in the atrial appendage.

FIG. 1 shows first, second, third and fourth prior art devices used to close or occlude a left atrial appendage. The first device 105 (also referred to as the PLAATO (Percutaneous Left Atrial Appendage Transcatheter Occlusion) device) consists of a self-expanding Nitinol cage 107 covered with polytetrafluoroethylene. Rows of anchors 108 along a circumference secure the cage 107 within the LAA ostium. The second device 110 (also referred to as the Watchman® device) has a self-expanding Nitinol frame with fixation anchors 112 and a permeable polyester fabric cover 114. The third device 115 (also referred to as the ACP (Amplatzer™ Cardiac Plug) device) is a self-expanding device composed of a Nitinol wire mesh and polyester patch and consists of a distal lobe 117 and a proximal disk 118 connected by a short central waist 116. The fourth device 120 (also referred to as the WaveCrest® device) has an umbrella shaped polytetrafluoroethylene cap 122 and a plurality of anchors 124.

Each of these prior art devices have shortcomings thereby suggesting that development is required for a more effective and widely acceptable LAA closure device. Most prior devices depend on a single post deployment shape and dimensions for adequate anchoring in the LAA, resulting in improper closure and premature dislodgement. Appropriate sizing is essential for adequate function of these devices. Also, all of these devices rely solely on the shape memory changes from the Nitinol cage for adequate sizing and fit and do not allow for an operator to adjust the shape or dimension or a pressure applied by the device on LAA wall post-deployment to adjust to individual LAA anatomy.

SUMMARY

The present specification discloses a device adapted to treat a left atrial appendage (LAA) of a patient, the device comprising: a tissue ingrowth member; a connector; a central member having distal and proximal ends, wherein the proximal end of the central member is positioned proximate a center of the tissue ingrowth member and the distal end of the central member is coupled to the connector; and a plurality of struts having distal and proximal ends, wherein the distal ends of the plurality of struts are coupled to a plurality of corresponding points along a surface of the tissue ingrowth member, and wherein the proximal ends of the plurality of struts are coupled to the connector; wherein said device is configurable between a pre-deployment configuration, a first post-deployment configuration, and a second post-deployment configuration, further wherein, when in said first post-deployment configuration, the device has at least one first dimension and applies a first pressure against a cardiac wall and when in said second post-deployment configuration, said device has at least one second dimension and applies a second pressure against the cardiac wall, wherein said at least one second dimension is greater than said at least one first dimension and said second pressure is greater than said first pressure.

Optionally, the central member is rigid and includes a plurality of extensions along its length, the extensions being unidirectional, and wherein the central member is configured to pass through the center of the tissue ingrowth member and the plurality of extensions is configured to engage and lock with the center of the tissue ingrowth member to lock the device in the second post-deployment configuration.

Optionally, the plurality of extensions comprises a plurality of barbs and each of the plurality of barbs has a sharp edge tapering in one direction.

Optionally, the central member is rigid and includes a screw connection mechanism comprising a first portion and a second portion, wherein said second portion is configured to be telescopically received within said first portion via screw threads on an outer surface of the second portion and an inner surface of the first portion, and further wherein said screw threads are configured to engage to lock said device in a post-deployment configuration. The screw mechanism connection can be adjusted to alter the post-deployment pressures for ideal deployment.

Optionally, the tissue ingrowth member has a substantially flat disc shape when in the second post-deployment configuration.

Optionally, portions of the distal ends of the plurality of struts extend beyond the surface of the tissue ingrowth member to form a plurality of anchors.

Optionally, the device is compressed into said pre-deployment configuration and configured to be positioned within, and delivered by, a catheter.

Optionally, the device further comprises a second connector attached at the center of the tissue ingrowth member and connected to a distal end of the central member, further wherein the central member comprises a shape memory alloy, is adapted to be collapsible and is configured to have a substantially linear shape when the device is in the pre-deployment configuration and a curved shape when the device is in the second post-deployment configuration.

Optionally, the central member is rigid and includes a plurality of phalanges along its length, the plurality of phalanges configured to change from a first configuration, in which the plurality of phalanges is flush with the central member, to a second configuration, in which the plurality of phalanges extends outwardly from the central member, and wherein the central member is configured to pass through the center of the tissue ingrowth member and the plurality of phalanges, once extended, is configured to engage and lock with the center of the tissue ingrowth member to lock the device in the second post-deployment configuration. Optionally, the plurality of phalanges is configured to be spring-loaded or magnetically actuated to change from the first configuration to the second configuration.

The present specification also discloses a device adapted to treat a left atrial appendage (LAA) of a patient, the device comprising: a tissue ingrowth member; a first connector and a second connector, wherein the second connector is positioned at a center of the tissue ingrowth member; a central member having distal and proximal ends, wherein the distal end of the central member is positioned proximate to the second connector and the proximal end of the central member is coupled to the first connector; at least one first strut having a distal end and a proximal end, wherein the distal end of the at least one first strut is coupled to at least one first corresponding point along a surface of the tissue ingrowth member, and wherein the proximal end of the at least one first strut is coupled to the second connector; and at least one second strut having a distal end and a proximal end, wherein the proximal end of the at least one second strut is coupled to at least one second corresponding point along a surface of the tissue ingrowth member, and wherein the distal end of the at least one second strut is coupled to the first connector; wherein the device is configurable between a pre-deployment configuration, a first post-deployment configuration, and a second post-deployment configuration, wherein, when in the first post-deployment configuration, the device has at least one first dimension and applies a first pressure against a cardiac wall and when in the second post-deployment configuration, the device has at least one second dimension and applies a second pressure against the cardiac wall, wherein the at least one second dimension is greater than the at least one first dimension and the second pressure is greater than the first pressure.

Optionally, the tissue ingrowth member has an umbrella shape when in the second post-deployment configuration and extends only between said second plurality of struts.

Optionally, a portion of the distal end of the at least one first strut extends beyond the at least one first corresponding point to form a first at least one first anchor and wherein a portion of the proximal end of the at least one second strut extends beyond the at least one second corresponding point to form at least one second anchor.

Optionally, the device is adapted to be compressed into the pre-deployment configuration and adapted to be positioned within a catheter.

Optionally, the central member is rigid and includes a plurality of barbs along its length, the barbs being unidirectional, and wherein the central member is configured to pass through the second connector and the plurality of barbs is configured to engage and lock with the second connector to lock the device in the second post-deployment configuration.

Optionally, a distal end of the central member is attached to the second connector and wherein the central member is composed of a shape memory alloy, collapsible and has a substantially straight shape when the device is in the pre-deployment configuration and a curved shape when the device is in the second post-deployment configuration.

Optionally, the central member is rigid and includes a plurality of phalanges along its length, said plurality of phalanges configured to change from a first configuration, wherein the plurality of phalanges is flush with said central member, to a second configuration, wherein said plurality of phalanges extends outwardly from said central member, and wherein the central member is configured to pass through said center of said tissue ingrowth member and said plurality of phalanges, once extended, is configured to engage and lock with said center of said tissue ingrowth member to lock said device in said second post-deployment configuration. Optionally, said plurality of phalanges is spring-loaded or magnetically actuated to change from said first configuration to said second configuration.

The present specification also discloses a method of using a device to close a left atrial appendage (LAA) in a patient, the method comprising: positioning the device in the LAA, wherein the device comprises a tissue ingrowth member, a connector, a central member having distal and proximal ends with the distal end of the central member positioned proximate a center of the tissue ingrowth member and the proximal end of the central member coupled to the connector, and a plurality of struts having distal and proximal ends with the distal ends of the plurality of struts coupled to a plurality of corresponding points along a circumference of the tissue ingrowth member and the proximal ends of the plurality of struts coupled to the connector, wherein the device is delivered in a pre-deployment configuration; and changing the device from the pre-deployment configuration to a first post-deployment configuration and then a second post-deployment configuration wherein, when in said first post-deployment configuration, the device has at least one first dimension and applies a first pressure against a cardiac wall and when in said second post-deployment configuration, said device has at least one second dimension and applies a second pressure against the cardiac wall, wherein said at least one second dimension is greater than said at least one first dimension and said second pressure is greater than said first pressure.

Optionally, the central member is rigid and includes a plurality of barbs along its length, said barbs being unidirectional, and wherein the central member is configured to pass through said center of the tissue ingrowth member and said plurality of barbs is configured to engage and lock with said center of the tissue ingrowth member to lock said device in said second post-deployment configuration.

Optionally, the device further comprises a second connector attached at said center of said tissue ingrowth member and connected to a distal end of said central member, wherein the central member is composed of a shape memory alloy, collapsible and has a substantially straight shape when the device is in said pre-deployment configuration and a curved shape when the device is in said second post-deployment configuration.

Optionally, the central member is rigid and includes a plurality of phalanges along its length, said plurality of phalanges configured to change from a first configuration, wherein the plurality of phalanges is flush with said central member, to a second configuration, wherein said plurality of phalanges extends outwardly from said central member, and wherein the central member is configured to pass through said center of said tissue ingrowth member and said plurality of phalanges, once extended, is configured to engage and lock with said center of said tissue ingrowth member to lock said device in said second post-deployment configuration.

Optionally, the device includes electrically conductive members configured to contact the LAA or LA surface wherein an electric current is passed through the electrical conductive members to ablate an LAA or LA tissue. Any one or more of the struts, connectors, extensions, barbs, tissue ingrowth members, connection points, or anchors may be configured to receive and deliver an electrical current to the cardiac tissue. The current can be monopolar or bipolar, radiofrequency current or current to induce electroporation in the LAA or LA tissue. The ablative effect can be used to ablate arrhythmogenic tissue proximate an LAA. The ablative effect can also be used to create fibrosis and help with anchoring of the LAA occlusion device.

The aforementioned and other embodiments of the present invention shall be described in greater depth in the drawings and detailed description provided below.

BRIEF DESCRIPTION OF THE DRAWINGS

These and other features and advantages of the present invention will be further appreciated, as they become better understood by reference to the detailed description when considered in connection with the accompanying drawings, wherein:

FIG. 1 shows first, second, third and fourth prior art LAA occlusion devices;

FIG. 3A shows a first wire-frame side view of an LAA occlusion device, in accordance with some embodiments of the present specification;

FIG. 3B shows a top view of the LAA occlusion device of FIG. 3A, in accordance with some embodiments of the present specification;

FIG. 3C shows a bottom view of the LAA occlusion device of FIG. 3A, in accordance with some embodiments of the present specification;

FIG. 3E shows a wire-frame side view of another LAA occlusion device, in accordance with some embodiments of the present specification;

FIG. 4E shows a wire-frame side view of the LAA an occlusion device comprising a screw mechanism for changing shapes, in accordance with some embodiments of the present specification;

FIG. 6D shows a perspective view of the LAA occlusion device of FIG. 6A in the first post-deployment shape, in accordance with some embodiments of the present specification;

FIG. 6H shows a side view of the LAA occlusion device of FIG. 6F in a second post-deployment shape, in accordance with some embodiments of the present specification;

FIG. 9 is a flowchart of a plurality of exemplary steps of a method of using an occlusion device to close an LAA, in accordance with some embodiments of the present specification.

DETAILED DESCRIPTION

Figure 2A:
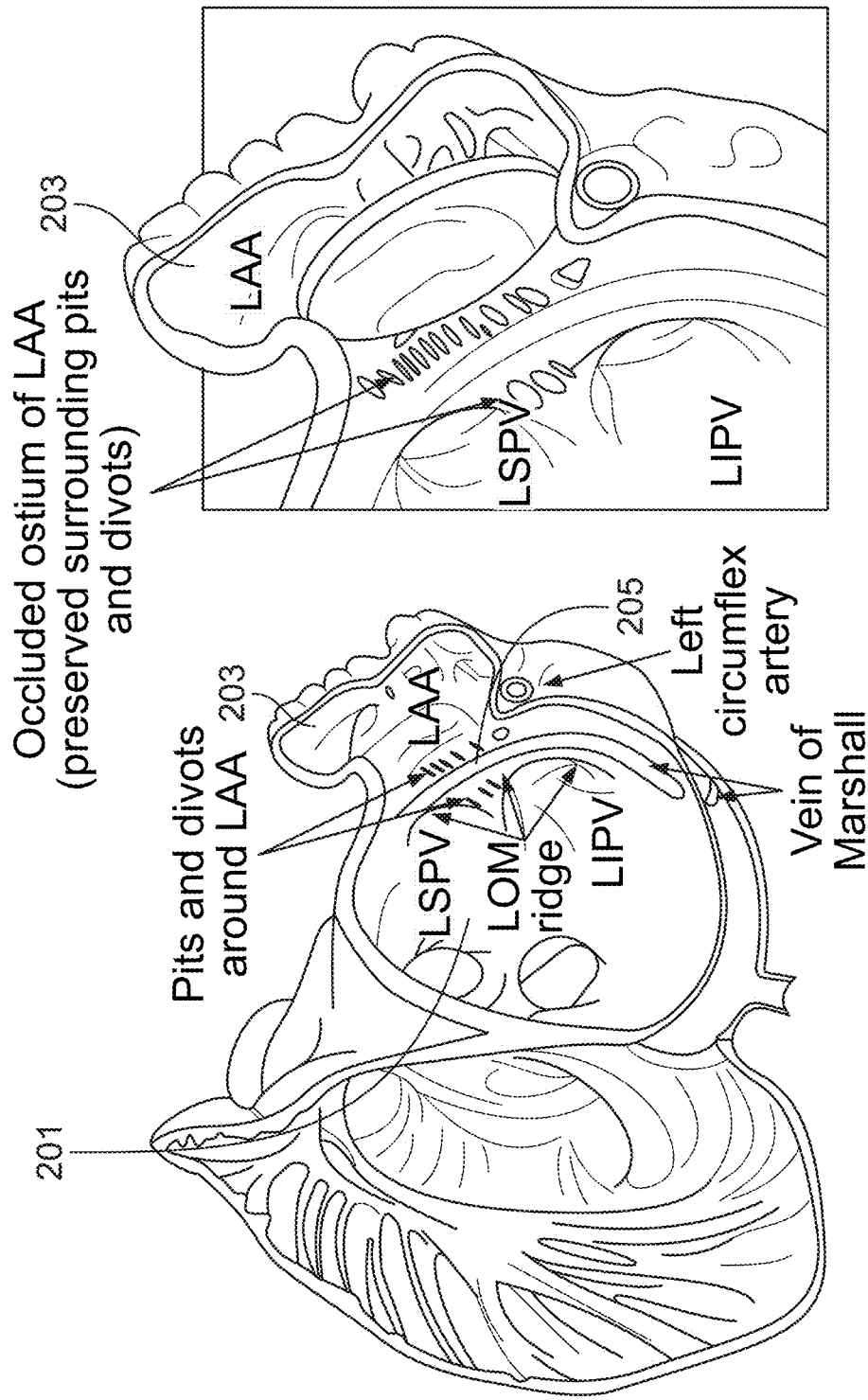
FIG. 2A illustrates a left atrium depicting a left atrial appendage in a wall of the left atrium.

"Treat," "treatment," and variations thereof refer to any reduction in the extent, frequency, or severity of one or more symptoms or signs associated with a condition.

"Duration" and variations thereof refer to the time course of a prescribed treatment, from initiation to conclusion, whether the treatment is concluded because the condition is resolved or the treatment is suspended for any reason. Over the duration of treatment, a plurality of treatment periods may be prescribed during which one or more prescribed stimuli are administered to the subject.

"Period" refers to the time over which a "dose" of stimulation is administered to a subject as part of the prescribed treatment plan.

The term "and/or" means one or all of the listed elements or a combination of any two or more of the listed elements.

In the description and claims of the application, each of the words "comprise" "include" and "have", and forms thereof, are not necessarily limited to members in a list with which the words may be associated. The terms "comprises" and variations thereof do not have a limiting meaning where these terms appear in the description and claims. It should be noted herein that any feature or component described in association with a specific embodiment may be used and implemented with any other embodiment unless clearly indicated otherwise.

Unless otherwise specified, "a," "an," "the," "one or more," and "at least one" are used interchangeably and mean one or more than one.

The term "controller" refers to an integrated hardware and software system defined by a plurality of processing elements, such as integrated circuits, application specific integrated circuits, and/or field programmable gate arrays, in data communication with memory elements, such as random access memory or read only memory where one or more processing elements are configured to execute programmatic instructions stored in one or more memory elements.

The term "cardiac tissue" refers to a portion of the pulmonary vein, a pulmonary vein ostium, a junction between the left atrium and pulmonary vein, an atrium, a left atrial appendage, tissue adjacent thereto, or other parts of the heart and adjacent tissue.

For any method disclosed herein that includes discrete steps, the steps may be conducted in any feasible order. And, as appropriate, any combination of two or more steps may be conducted simultaneously.

Also herein, the recitations of numerical ranges by endpoints include all numbers subsumed within that range (e.g., 1 to 5 includes 1, 1.5, 2, 2.75, 3, 3.80, 4, 5, etc.). Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present specification. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the specification are approximations, the numerical values set forth in the specific examples are reported as precisely as possible. All numerical values, however, inherently contain a range necessarily resulting from the standard deviation found in their respective testing measurements.

It should be appreciated that the devices and embodiments described herein are implemented in concert with a controller that comprises a microprocessor executing control instructions. The controller can be in the form of any computing device, including desktop, laptop, and mobile device, and can communicate control signals to the devices in wired or wireless form.

The present invention is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

Figure 2B:
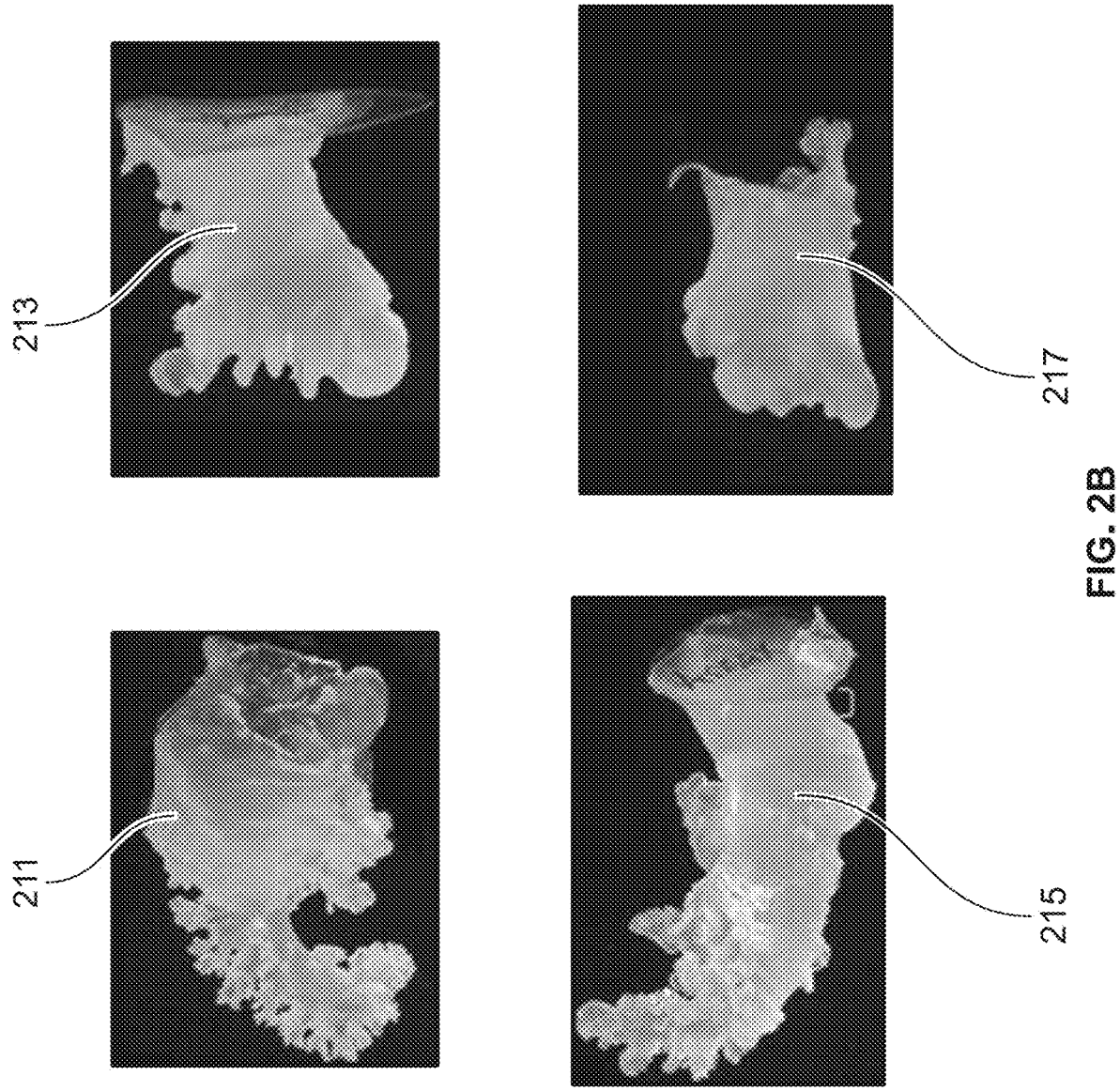
FIG. 2B illustrates a plurality of left atrial appendages.

FIG. 2A illustrates a left atrium 201 depicting a left atrial appendage 203 in a wall 205 of the left atrium 201. FIG. 2B illustrates a plurality of left atrial appendages 211, 213, 215, 217 depicting a variety of shapes of the left atrial appendages 211, 213, 215, 217.

First Embodiment

Figure 3D:
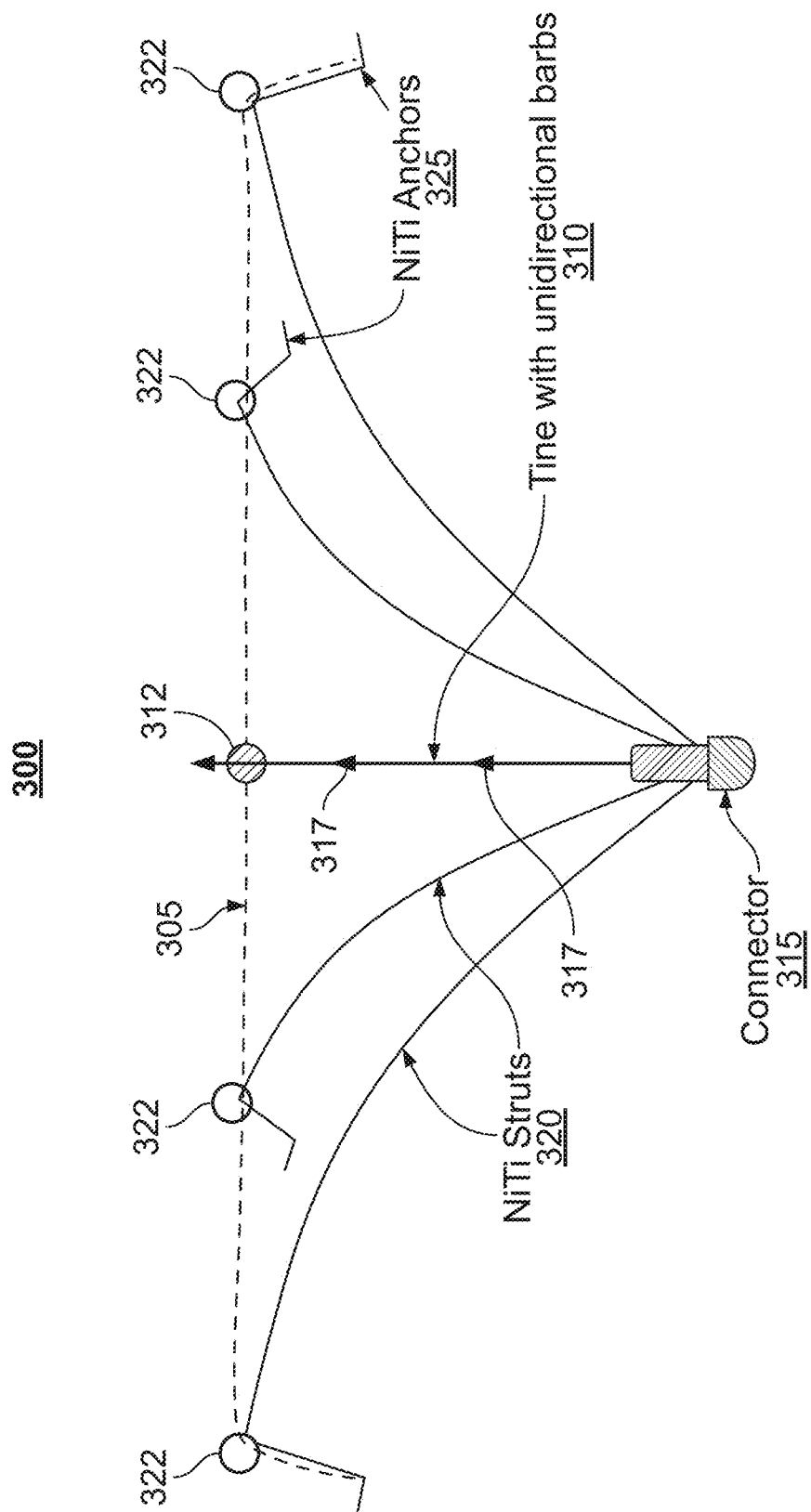
FIG. 3D shows a second wire-frame side view of the LAA occlusion device of FIG. 3A, in accordance with some embodiments of the present specification.

FIGS. 3A and 3D show wire-frame side views, FIG. 3B shows a top view and FIG. 3C shows a bottom view of an LAA (Left Atrial Appendage) occlusion device 300 in a fully deployed configuration, in accordance with some embodiments of the present specification. Referring now to FIGS. 3A through 3D simultaneously, the device 300 has a tissue ingrowth member 305 that assumes a shape of a substantially circular or flat disc when the device 300 is in a fully expanded state. In some embodiments, the tissue ingrowth member 305 is a mesh, cage or web of wires. In some embodiments, the tissue ingrowth member 305 is a fabric cover. In some embodiments, the tissue growth member 305 is coated with extracellular matrix (ECM) or another biological material to promote tissue ingrowth. A distal end of a rigid central member, or tine, 310 is movably positioned within a center 312 of the substantially circular or disc shaped tissue ingrowth member 305 while a proximal end of the tine 310 is coupled to a connector 315. In some embodiments, the tine 310 includes a plurality of unidirectional extensions or barbs 317 along its length.

Distal ends of a plurality of struts 320 are connected, coupled or attached to a plurality of connection points 322 along the circumference of the substantially circular or disc shaped tissue ingrowth member 305 while proximal ends of the plurality of struts 320 are coupled to the connector 315. Portions of the distal tips of the plurality of struts 320 extend beyond their respective connection points 322 of attachment to form a plurality of anchors 325. In some embodiments, the distal tips forming the anchors 325 are angled or bent with respect to a substantially horizontal plane of the tissue ingrowth member 305.

In some embodiments, the tine 310, the barbs 317 and the plurality of struts 320 are wires of a shape memory material such as, for example, Nitinol. As the device 300 changes shape from its pre-deployment configuration to its first post-deployment configuration, the rigid tine 310 extends through the center 312. The first pre-deployment shape applies a first pressure on the LAA wall and the optional anchors 325 pierce the LAA wall to a first depth. In the first post-deployment position the operator has ability to adjust or reposition the LAA occlusion device 300 proximate an LAA. Once the operator is satisfied with the position of the LAA occlusion device 300, the operator applies a pull or tension on the tine 310 pulling it through the center 312, engage the unidirectional barbs 317 with the center 312. This pulls allows the LAA occlusion device 300 to assume its $2^{nd}$ post-deployment position applying a $2^{nd}$ pressure on the LAA wall and the optional anchors 325 pierce the LAA wall to a $2^{nd}$ depth. In the $2^{nd}$ post-deployment, the LAA occlusion device 300 is secured to the LAA wall in its final therapeutic position/configuration. The central tine 310 may have multiple unidirectional barbs 317, allowing for multiple $2^{nd}$ post-deployment positions dependent an individual patient and individual LAA anatomy. In embodiments, once the LAA occlusion device 300 is deployed, the tissue ingrowth member 305 faces the left atrial chamber and the connector 315 and struts 320 sit in the LAA cavity.

Second Embodiment

Figure 3F:
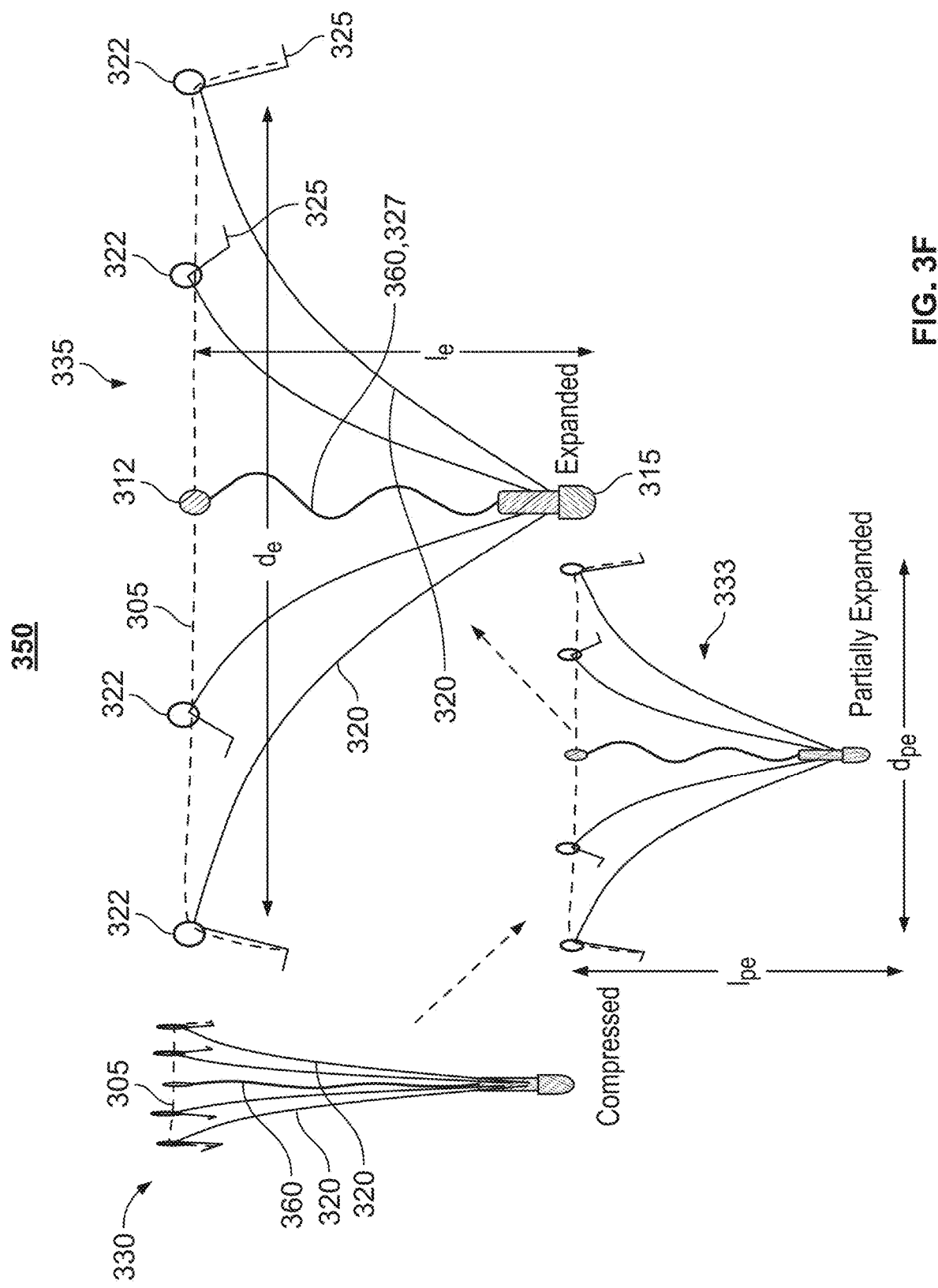
FIG. 3F shows pre-deployment and post-deployment shapes of the LAA occlusion device of FIG. 3E, in accordance with some embodiments of the present specification.

FIG. 3E shows a wire-frame side views while FIG. 3F shows pre-deployment and post-deployment shapes of another LAA occlusion device 350, in accordance with embodiments of the present specification. The device 350 of FIGS. 3E and 3F is similar to that of FIGS. 3A-3D, with the difference of the rigid central member, or tine, 310 in the device 300 of FIGS. 3A-3D being replaced with a collapsible central member, or tine, 360 in the device 350 of FIGS. 3E and 3F. The distal end of the collapsible tine 360 is connected to the center 312. The collapsible tine is made of SMA and over time changes from a relatively straight pre-deployment position to relatively coiled post-deployment position wherein the $2^{nd}$ post-deployment pressure slowly increases over time post-deployment and the anchors 325 embed deeper into the LAA wall over time, post-deployment.

Referring to FIGS. 3E and 3F, prior to deployment, the tine 360 maintains a substantially straight configuration. However, post deployment, the tine 360 changes its shape from a substantially straight to a coiled or curved configuration 327, as shown in FIGS. 3E and 3F. Modulation of the shape of the tine 360, from the substantially straight configuration to the coiled or curved configuration, pulls the connector 315 toward the tissue ingrowth member 305, thereby expanding the plurality of struts 320 and burying the plurality of anchors 325 into the endocardium/myocardium of a patient's heart. In embodiments, the tine 360 of FIGS. 3E and 3F does not include barbs.

Figure 7:
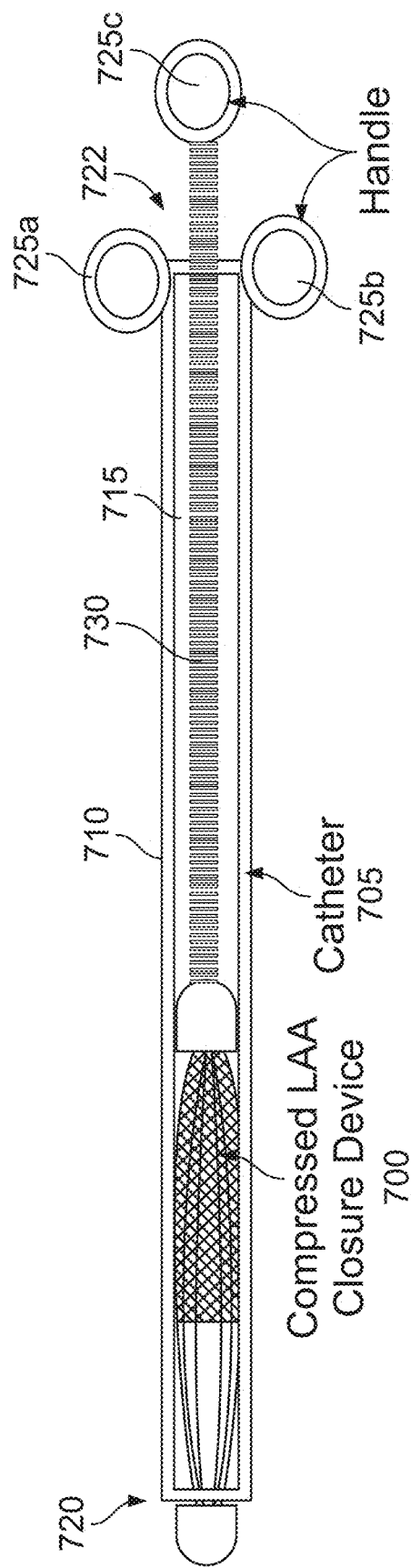
FIG. 7 shows a catheter for deploying an LAA occlusion device into a left atrium of a patient's heart, in accordance with some embodiments of the present specification.

Referring to FIG. 3F, the device 350 is configured into a pre-deployment shape 330 wherein the device 350 is compressed and positioned within a catheter, such as the catheter 705 of FIG. 7. The device 350 assumes a first post-deployment shape 333 such that the device 350 is partially expanded upon being released from the catheter. Finally, the device 350 transitions to a second post-deployment shape 335 wherein the device 350 is fully expanded due to the tine 360 shaping from the substantially straight configuration to the coiled or curved configuration.

In some embodiments, the second post-deployment shape 335 has at least one first expanded dimension '$d_e$' that is greater than a corresponding first compressed dimension '$d_{pe}$' of the first post-deployment shape 333. In some embodiments, the second post-deployment shape 335 has at least one second expanded dimension '$l_e$' that is less than a corresponding second compressed dimension '$l_{pe}$' of the first post-deployment shape 333. In some embodiments, the second post-deployment shape 335 has at least one second expanded dimension '$d_e$' that is greater than a corresponding second compressed dimension '$d_{pe}$' of the first post-deployment shape 333. In the first post-deployment shape 333, the device 350 exerts a first pressure on the LAA wall while in the second post-deployment shape 335, the device 350 exerts a second pressure on the LAA wall. In some embodiments, the first pressure on the LAA wall is less than the second pressure on the LAA wall. The anchors 325 have a first position in the first post-deployment shape and a second position in the second post-deployment shape. In embodiments, in the second position, the anchors 325 pierce the LAA wall deeper than they do when in the first position.

Third Through Eighth Embodiments

Figure 4A:
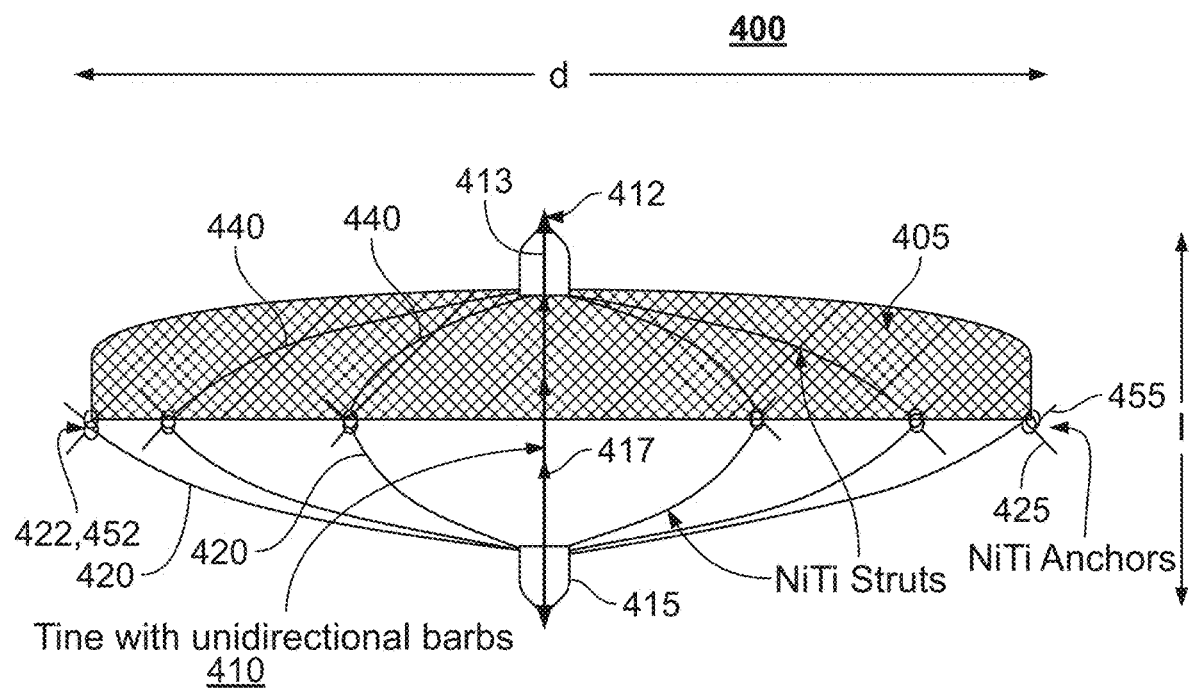
FIG. 4A shows a wire-frame side view of another LAA occlusion device, in accordance with some embodiments of the present specification.
Figure 4B:
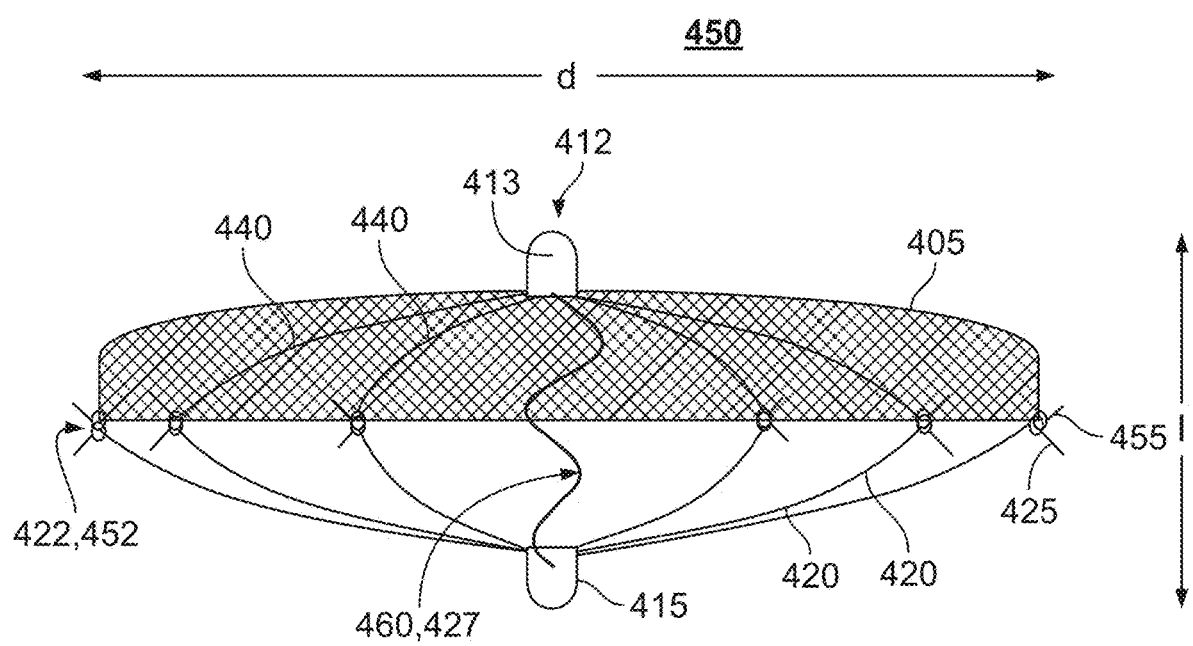
FIG. 4B shows a wire-frame side view of the LAA yet another occlusion device, in accordance with some embodiments of the present specification.

FIG. 4A shows a wire-frame side view of another LAA occlusion device 400, in accordance with some embodiments of the present specification. FIG. 4B shows a wire-frame side view of yet another LAA occlusion device 450, in accordance with some embodiments of the present specification. Referring to FIGS. 4A and 4B simultaneously, the devices 400, 450 comprise a tissue ingrowth member 405 that assumes a shape of an umbrella or inverted cap when the devices 400, 450 are in a fully expanded state, as depicted in FIGS. 4A and 4B. In some embodiments, the tissue ingrowth member 405 is a mesh, cage or web of wires. In some embodiments, the tissue ingrowth member 405 is a membrane or a fabric cover. In some embodiments, the tissue ingrowth member 405 is coated with extracellular matrix (ECM) or another biological material to promote tissue ingrowth. Referring to FIG. 4A, a distal end of a rigid central member, or tine, 410 is movably positioned within a first connector 413 positioned at a center 412 of the tissue ingrowth member 405 while a proximal end of the tine 410 is coupled to a second connector 415. The tine 410 includes a plurality of unidirectional extensions or barbs 417 along its length. In some embodiments, as the device 400 changes shape from its pre-deployment configuration to its post-deployment configuration, the rigid tine 410 extends through the first connector 413 and the barbs 417 engage with the first connector 413, locking the device in the post-deployment configuration. In some embodiments, as the device 400 changes shape from its pre-deployment configuration to its post-deployment configuration, the rigid tine 410 extends through the first connector 413 and center 412 and punctures the epicardium/myocardium of the patient's heart, assisting in holding the device in place.

Referring to FIG. 4B, the device 450 comprises a collapsible tine 460 in place of a rigid tine and the distal end of the collapsible tine 460 is connected to the second connector 413. Prior to deployment, the tine 460 is in a substantially straight configuration. Post deployment, the tine 460 changes its shape from substantially straight to a coiled or curved configuration 427, as shown in FIG. 4B. Extension of the rigid tine 410 through said center 412 and said second connector 413, as with the device 400 depicted in FIG. 4A, or modulation of the shape of the tine 460, from a substantially straight configuration to the coiled or curved configuration 427, as with the device 450 depicted in FIG. 4B, pulls the first and second connectors 413, 415 toward each other thereby, expanding the first and second plurality of struts 420, 440 and burying the first and second plurality of anchors 425, 455 into the endocardium/myocardium of a patient's heart.

Distal ends of a first plurality of struts 420 are connected, coupled or attached to a first plurality of connection points 422 along a circumference of the umbrella or inverted bowl shaped tissue ingrowth member 405 while proximal ends of the first plurality of struts 420 are coupled to the second connector 415. Portions of the distal tips of the first plurality of struts 420 extend beyond their respective connection points 422 of attachment to form a first plurality of anchors 425. In some embodiments, the distal tips forming the first plurality of anchors 425 are angled or bent with respect to a substantially horizontal plane of the tissue ingrowth member 405.

Proximal ends of a second plurality of struts 440 are connected, coupled or attached to a second plurality of connection points 452 along a circumference of the umbrella or inverted bowl shaped tissue ingrowth member 405 while distal ends of the second plurality of struts 440 are coupled to the first connector 413. In embodiments, the tissue ingrowth member 405 is positioned on a side of the devices 400, 400 having only the second plurality of struts 440.

Portions of the proximal tips of the second plurality of struts 440 extend beyond their respective connection points 452 of attachment to form a second plurality of anchors 455. In some embodiments, the proximal tips forming the second plurality of anchors 455 are angled or bent with respect to the substantially horizontal plane of the tissue ingrowth member 405. In some embodiments, the positioning of the first plurality of connection points 422 coincides with the positioning of the second plurality of connection points 452 of attachment. In alternate embodiments, the positioning of the first plurality of connection points 422 does not coincide with the positioning of the second plurality of connection points 452 of attachment.

In some embodiments, the tines 410, 460, the barbs 417 and the first and second plurality of struts 420, 440 are wires of a shape memory material such as, for example, Nitinol.

In embodiments, the devices 400, 450 are configured into a pre-deployment shape wherein the device 400 is compressed and positioned within a catheter, such as the catheter 705 of FIG. 7. The devices 400, 450 assume a first post-deployment shape such that the devices 400, 450 are partially expanded upon being released from the catheter. Finally, the devices 400, 450 transition to a second post-deployment shape wherein the devices 400, 450 are fully expanded. In some embodiments, when in the second post-deployment shape, the first connector 412 and second 415 connector are positioned closer together than when in the first post-deployment shape and a transverse dimension "d" of the LAA occlusion device when in the second post-deployment shape is greater than when in the first post-deployment shape, exerting a greater pressure across at least 50% of a transverse circumference of the device.

In some embodiments, the second post-deployment shape has at least one dimension 'd' that is greater than the first post-deployment shape. In some embodiments, the second post-deployment shape has at least one dimension 'l' that is less than the first post-deployment shape. In the first post-deployment shape the devices 400, 450 exert a first pressure on the LAA wall while in the second post-deployment shape the devices 400, 450 exert a second pressure on the LAA wall. In some embodiments, the first pressure on the LAA wall is less than the second pressure on the LAA wall. The first and second plurality of anchors 425, 455 have a first position in the first post-deployment shape and a second position in the second post-deployment shape. In embodiments, in the second position the first and second plurality of anchors 425, 455 pierce the LAA wall deeper than they do when in the first position. In embodiments, once implanted, the devices 400, 450 are positioned such that the tissue ingrowth member 405 faces the left atrium while an opposite side of the devices 400, 450, comprising the first plurality of struts 420, with no tissue ingrowth member between said struts 420, is positioned facing an LAA of the patient and resides within the LAA of the patient.

Figure 4C:
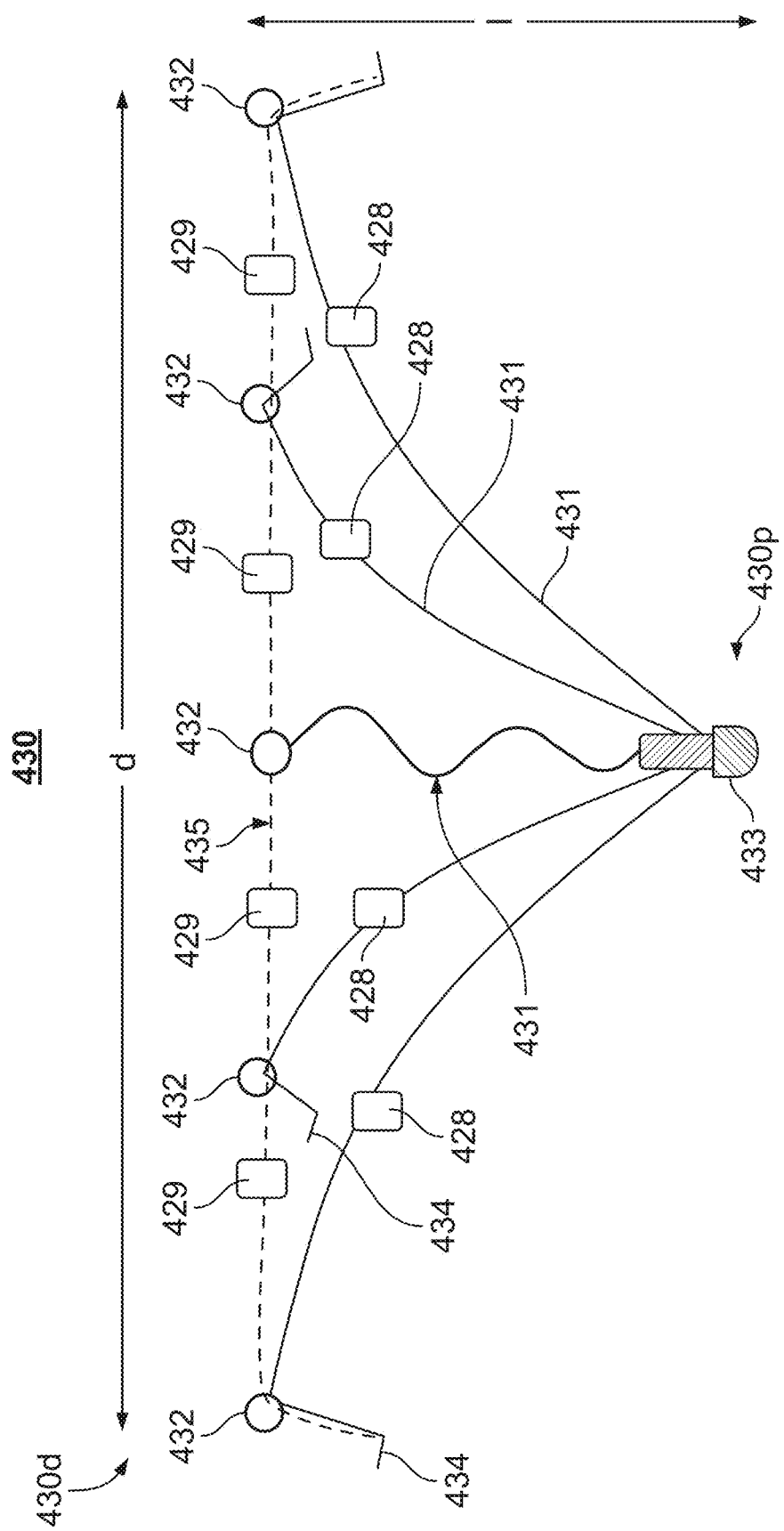
FIG. 4C shows a wire-frame side view of the LAA an occlusion device with magnets, in accordance with some embodiments of the present specification.
Figure 4D:
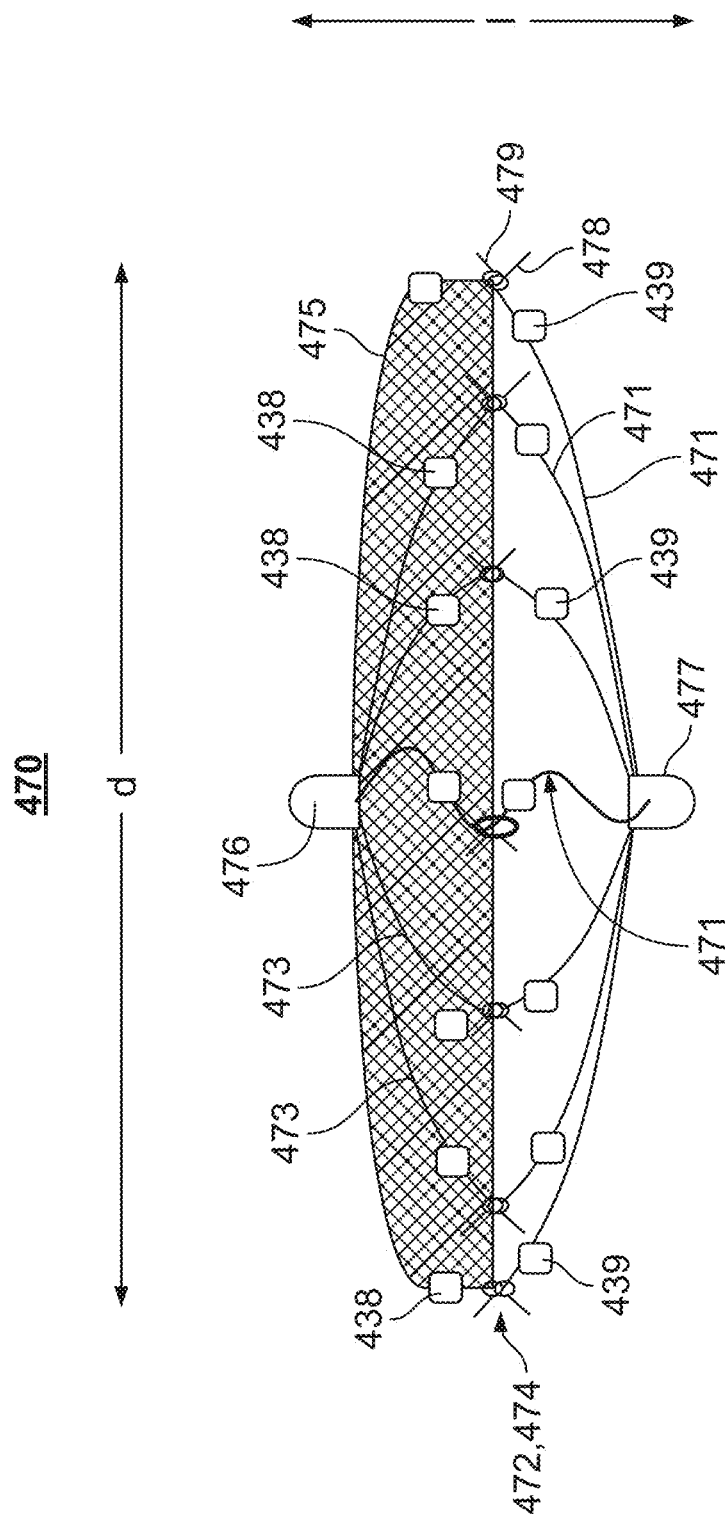
FIG. 4D shows a wire-frame side view of the LAA another occlusion device with magnets, in accordance with some embodiments of the present specification.

In other embodiments, as shown in FIGS. 4C and 4D, the shape change from the first post-deployment shape to the second post-deployment shape is be achieved by using magnetic force. In some embodiments, a first set of magnets 428, 438 is positioned at a proximal end 430p, 470p of the device 430, 470 and a second set of magnets 429, 439 is positioned at a distal end 430d, 470d of the device 430, 470. Magnetic forces between the first set of magnets 428, 438 and the second set of magnets 429, 439 results in drawing the proximal end and distal end of the device 430, 470 together, compressing the dimension "l" of the device and increasing the dimension "d" of the device, which causes an increase in a post-deployment pressure/force on the LAA wall to keep the device in position. The final post-deployment pressure is determined by the attractive force between the 2 sets of magnets. In some embodiments, the pressure and the attractive force between the magnets increases post-deployment over time until the pressure reaches a final pressure at which time the device becomes anchored in an LAA.

Referring now to FIG. 4C, the device 430 has a tissue ingrowth member 435 that assumes a shape of a substantially circular or flat disc when the device 430 is in a fully expanded state. In some embodiments, the tissue ingrowth member 435 is a mesh, cage or web of wires. In some embodiments, the tissue ingrowth member 435 is a fabric cover. In some embodiments, the tissue growth member 435 is coated with extracellular matrix (ECM) or another biological material to promote tissue ingrowth.

Distal ends of a plurality of struts 431 are connected, coupled or attached to a plurality of connection points 432 along the circumference of the substantially circular or disc shaped tissue ingrowth member 435 while proximal ends of the plurality of struts 431 are coupled to a connector 433. Portions of the distal tips of the plurality of struts 431 extend beyond their respective connection points 432 of attachment to form a plurality of anchors 434. In some embodiments, the distal tips forming the anchors 434 are angled or bent with respect to a substantially horizontal plane of the tissue ingrowth member 435. In some embodiments, the first set of magnets 428 and the second set of magnets 429 comprise a number of magnets in a range of 1 to 20. In some embodiments, the first set of magnets 428 is positioned on the plurality of struts 431. In other embodiments, the first set of magnets 428 is positioned on the connector 433. In some embodiments, the second set of magnets 429 is positioned on the tissue ingrowth member 435.

In some embodiments, the plurality of struts 431 are wires of a shape memory material such as, for example, Nitinol. In embodiments, once the LAA occlusion device 430 is deployed, the tissue ingrowth member 435 faces the left atrial chamber and the connector 433 and struts 431 sit in the LAA cavity.

Referring now to FIG. 4D, the devices 470 comprises a tissue ingrowth member 475 that assumes a shape of an umbrella or inverted cap when the device 470 is in a fully expanded state. In some embodiments, the tissue ingrowth member 475 is a mesh, cage or web of wires. In some embodiments, the tissue ingrowth member 475 is a membrane or a fabric cover. In some embodiments, the tissue ingrowth member 475 is coated with extracellular matrix (ECM) or another biological material to promote tissue ingrowth. Distal ends of a first plurality of struts 471 are connected, coupled or attached to a first plurality of connection points 472 along a circumference of the umbrella or inverted bowl shaped tissue ingrowth member 475 while proximal ends of the first plurality of struts 471 are coupled to a second connector 477. Portions of the distal tips of the first plurality of struts 471 extend beyond their respective connection points 472 of attachment to form a first plurality of anchors 478. In some embodiments, the distal tips forming the first plurality of anchors 478 are angled or bent with respect to a substantially horizontal plane of the tissue ingrowth member 475.

Proximal ends of a second plurality of struts 473 are connected, coupled or attached to a second plurality of connection points 474 along a circumference of the umbrella or inverted bowl shaped tissue ingrowth member 475 while distal ends of the second plurality of struts 473 are coupled to a first connector 476. In embodiments, the tissue ingrowth member 475 is positioned on a side of the device 470 having only the second plurality of struts 473. Portions of the proximal tips of the second plurality of struts 473 extend beyond their respective connection points 474 of attachment to form a second plurality of anchors 479. In some embodiments, the proximal tips forming the second plurality of anchors 479 are angled or bent with respect to the substantially horizontal plane of the tissue ingrowth member 475. In some embodiments, the positioning of the first plurality of connection points 472 coincides with the positioning of the second plurality of connection points 474 of attachment. In alternate embodiments, the positioning of the first plurality of connection points 472 does not coincide with the positioning of the second plurality of connection points 474 of attachment. In some embodiments, the first set of magnets 438 and the second set of magnets 439 comprise a number of magnets in a range of 1 to 20. In some embodiments, the first set of magnets 438 is positioned on the first plurality of struts 471. In other embodiments, the first set of magnets 438 is positioned on the second connector 477. In some embodiments, the second set of magnets 439 is positioned on the second plurality of struts 473. In other embodiments, the second plurality of magnets 439 is positioned on the first connector 476. In some embodiments, the first and second plurality of struts 471, 473 are wires of a shape memory material such as, for example, Nitinol.

Figure 4F:
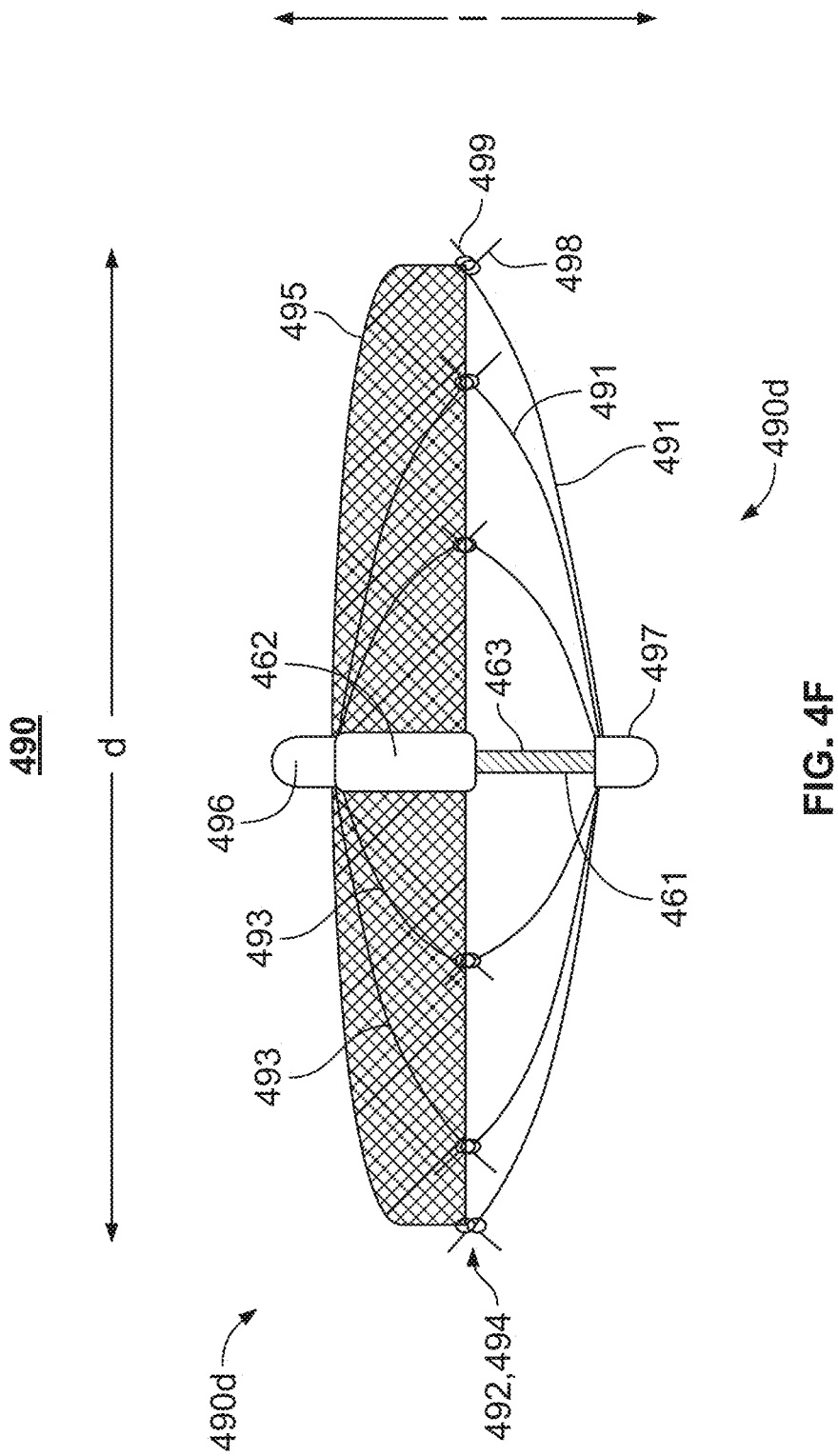
FIG. 4F shows a wire-frame side view of the LAA another occlusion device comprising a screw mechanism for changing shapes, in accordance with some embodiments of the present specification.

In other embodiments, as shown in FIGS. 4E and 4F, a screw connection mechanism 431 between a proximal end 480p, 490p of the device 480, 490 and a distal end 480d, 490d of the device 480, 490 is used to modify a length "l" and a diameter "d" of the device 480, 490 to attain a desirable end pressure optimal for device stabilization and anchoring. In embodiments, the screw connection mechanism 461 is rigid and comprises a first portion 462 configured to axially receive a second portion 463. The second portion 463 includes screw threads on its outer surface to securely connect with an inner threaded surface of the first portion 462. The second portion 463 may be telescopically advanced into and out of the first portion 462 via a turning motion to change the length "l" of the device 480, 490. Engaging the screw threads of the outer surface of the second portion 463 with the screw threads of the inner surface of the first portion 461 at a certain depth of the second portion 463 within the first portion 461 locks the device 480, 490 at a desired length "l". The screw connection mechanism 461 allows a user to titrate these parameters in a controllable fashion to meet individualized LAA anatomy. Pre, intra and post-procedure imaging can be used to ascertain the required dimension and fit.

Referring now to FIG. 4E, the device 480 has a tissue ingrowth member 485 that assumes a shape of a substantially circular or flat disc when the device 480 is in a fully expanded state. In some embodiments, the tissue ingrowth member 485 is a mesh, cage or web of wires. In some embodiments, the tissue ingrowth member 485 is a fabric cover. In some embodiments, the tissue growth member 485 is coated with extracellular matrix (ECM) or another biological material to promote tissue ingrowth.

Distal ends of a plurality of struts 481 are connected, coupled or attached to a plurality of connection points 482 along the circumference of the substantially circular or disc shaped tissue ingrowth member 485 while proximal ends of the plurality of struts 481 are coupled to a connector 483. Portions of the distal tips of the plurality of struts 481 extend beyond their respective connection points 482 of attachment to form a plurality of anchors 484. In some embodiments, the distal tips forming the anchors 484 are angled or bent with respect to a substantially horizontal plane of the tissue ingrowth member 485. In some embodiments, a first end of the first portion 462 of the screw connection mechanism 461 is attached to the tissue ingrowth member 485 at a connection point 488 and a second end of the first portion 462 of the screw connection mechanism 461 receives a first end of the second portion 463 of the screw connection mechanism 461. A second end of the second portion 463 of the screw connection mechanism 461 is attached to the connector 483. In embodiments, the connector 483 and second portion 463 of the screw connection mechanism 461 may be rotated to advance the second portion 463 into and out of the first portion 462 to change the length "l" of the device 480. In other embodiments, connection point 488 and/or the first portion 462 of the screw connection mechanism 461 may be rotated to advance the second portion 463 into and out of the first portion 462 to change the length "l" of the device 480.

In some embodiments, the plurality of struts 471 are wires of a shape memory material such as, for example, Nitinol. In embodiments, once the LAA occlusion device 480 is deployed, the tissue ingrowth member 485 faces the left atrial chamber and the connector 483 and struts 481 sit in the LAA cavity.

Referring now to FIG. 4F, the devices 490 comprises a tissue ingrowth member 495 that assumes a shape of an umbrella or inverted cap when the device 490 is in a fully expanded state. In some embodiments, the tissue ingrowth member 495 is a mesh, cage or web of wires. In some embodiments, the tissue ingrowth member 495 is a membrane or a fabric cover. In some embodiments, the tissue ingrowth member 495 is coated with extracellular matrix (ECM) or another biological material to promote tissue ingrowth. Distal ends of a first plurality of struts 491 are connected, coupled or attached to a first plurality of connection points 492 along a circumference of the umbrella or inverted bowl shaped tissue ingrowth member 495 while proximal ends of the first plurality of struts 491 are coupled to a second connector 497. Portions of the distal tips of the first plurality of struts 491 extend beyond their respective connection points 492 of attachment to form a first plurality of anchors 498. In some embodiments, the distal tips forming the first plurality of anchors 498 are angled or bent with respect to a substantially horizontal plane of the tissue ingrowth member 495.

Proximal ends of a second plurality of struts 493 are connected, coupled or attached to a second plurality of connection points 494 along a circumference of the umbrella or inverted bowl shaped tissue ingrowth member 495 while distal ends of the second plurality of struts 493 are coupled to a first connector 496. In embodiments, the tissue ingrowth member 495 is positioned on a side of the device 490 having only the second plurality of struts 493. Portions of the proximal tips of the second plurality of struts 493 extend beyond their respective connection points 494 of attachment to form a second plurality of anchors 499. In some embodiments, the proximal tips forming the second plurality of anchors 499 are angled or bent with respect to the substantially horizontal plane of the tissue ingrowth member 495. In some embodiments, the positioning of the first plurality of connection points 492 coincides with the positioning of the second plurality of connection points 494 of attachment. In alternate embodiments, the positioning of the first plurality of connection points 492 does not coincide with the positioning of the second plurality of connection points 494 of attachment. In some embodiments, a first end of the first portion 462 of the screw connection mechanism 461 is attached to the first connector 496 and a second end of the first portion 462 of the screw connection mechanism 461 receives a first end of the second portion 463 of the screw connection mechanism 461. A second end of the second portion 463 of the screw connection mechanism 461 is attached to the second connector 497. In embodiments, the second connector 497 and second portion 463 of the screw connection mechanism 461 may be rotated to advance the second portion 463 into and out of the first portion 462 to change the length "l" of the device 490. In other embodiments, first connector 496 and the first portion 462 of the screw connection mechanism 461 may be rotated to advance the second portion 463 into and out of the first portion 462 to change the length "l" of the device 490. In some embodiments, the first and second plurality of struts 471, 473 are wires of a shape memory material such as, for example, Nitinol.

Ninth Embodiment

Figure 5:
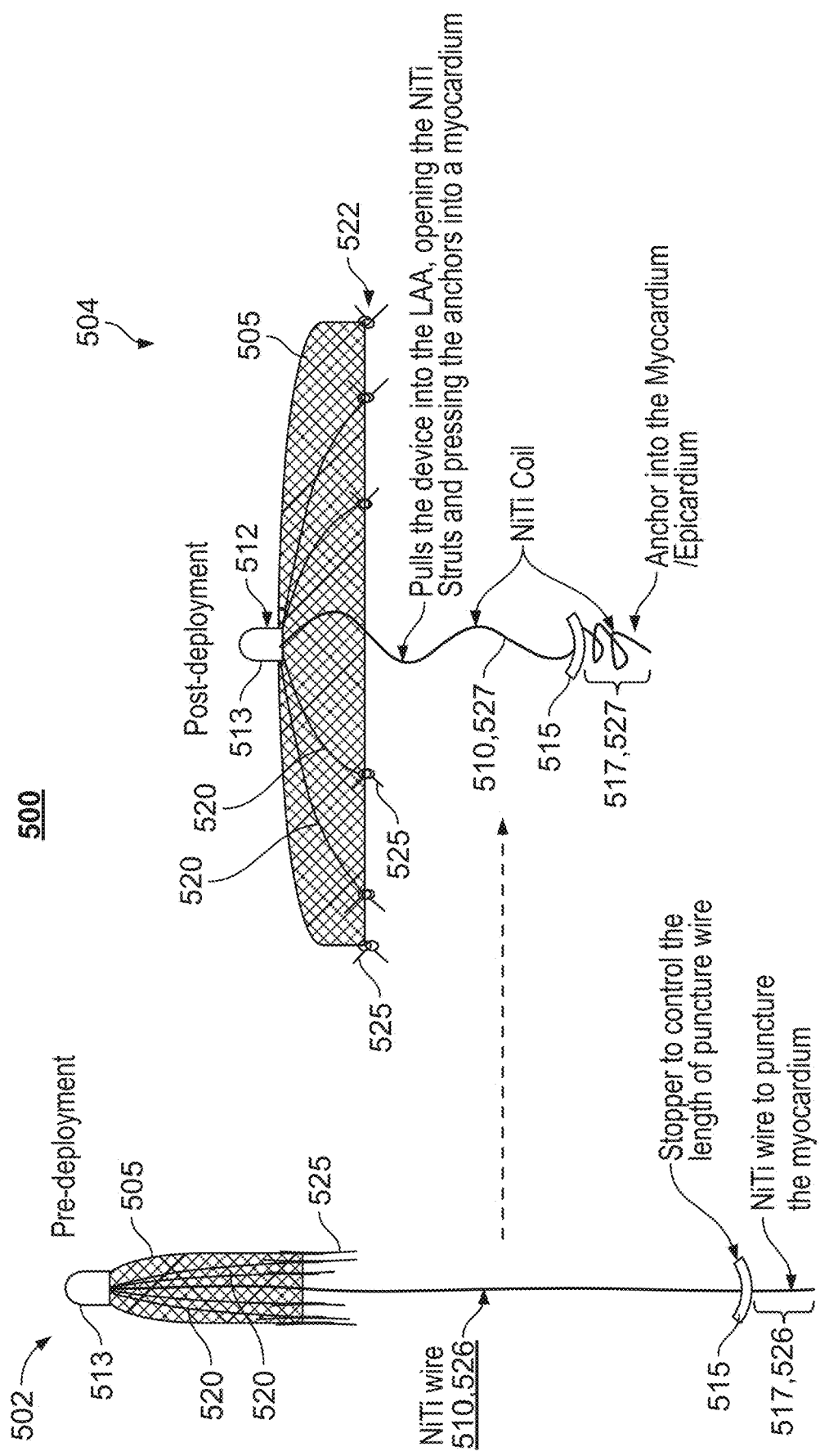
FIG. 5 shows wire-frame side views of another LAA occlusion device in pre-deployment and post-deployment shapes, in accordance with some embodiments of the present specification.

FIG. 5 shows wire-frame side views of an LAA occlusion device 500 in pre-deployment and post-deployment shapes 502, 504, in accordance with some embodiments of the present specification. The device 500 has a tissue ingrowth member 505 that assumes a shape of an umbrella or an inverted bowl when the device 500 is in a fully expanded state. In some embodiments, the tissue ingrowth member 505 is a mesh, cage or web of wires. In some embodiments, the tissue ingrowth member 505 is a membrane or a fabric cover. A proximal end of a tine 510 is connected, coupled or attached to a connector 513 at a center 512 of the tissue ingrowth member 505. A stopper 515 is connected proximate a distal end of the tine 510. A portion 517 of the distal end of the tine 510 extends distally and beyond the stopper 515 to puncture and anchor/lodge into the epicardium/myocardium of a patient's heart and specifically an LAA. The stopper 515 is used to control a length of the portion 517. In one embodiment the tine 510 and the portion 517 is made of an SMA which changes from a relatively straight position to a relatively coiled position. In some embodiments, the tine 510 includes a plurality of unidirectional extensions or barbs along its length on the portion 517 distal to the stopper 515.

Distal ends of a plurality of struts 520 are connected, coupled or attached to a plurality of connection points 522 along a circumference of the umbrella or inverted bowl shaped surface 505 while proximal ends of the plurality of struts 520 are coupled to the connector 513. Portions of the distal tips of the plurality of struts 520 extend beyond their respective connection points 522 of attachment to form a plurality of anchors 525. In some embodiments, the distal tips forming the anchors 525 are angled or bent with respect to a substantially horizontal plane of the tissue ingrowth member 505.

In some embodiments, the tine 510, barbs, and the plurality of struts 520 are wires of a shape memory material such as, for example, Nitinol.

Prior to deployment, the tine 510 and the portion 517 remain in a substantially straight configuration 526. However, post deployment, the tine 510 and the portion 517 change shapes from their respective substantially straight configurations 526 to coiled or curved configurations 527. During deployment, the portion 517 is used to puncture the epicardium/myocardium in an LAA. Post-deployment, the portion 517 coils up and anchors or lodges into the epicardium/myocardium of the LAA. Subsequently, modulation of the shape of the tine 510 and the lodged portion 517, from the substantially straight configuration 526 to the coiled or curved configuration 527, pulls the device 500 into the LAA thereby further expanding or opening the plurality of struts 520 and burying or pressing the plurality of anchors 525 into the epicardium/myocardium of the LAA.

In embodiments, the device 500 is configured into a pre-deployment shape 502 wherein the device 500 is compressed and positioned within a catheter, such as the catheter 705 of FIG. 7. The device 500 assumes a first post-deployment shape such that the device 500 is partially expanded upon being released from the catheter. Finally, the device 500 transitions to a second post-deployment shape 504 wherein the device 500 is fully expanded due to the tine 510 and the lodged portion 517 shaping from the substantially straight configurations to the coiled or curved configurations.

In some embodiments, the second post-deployment shape 504 has at least one dimension that is greater than the first post-deployment shape 502. In some embodiments, the second post-deployment shape 504 has at least one dimension that is lesser than the first post-deployment shape 502. In the first post-deployment shape 502 the device 500 exerts a first pressure on the LAA wall while in the second post-deployment shape 504 the device 500 exerts a second pressure on the LAA wall. In some embodiments, the first pressure on the LAA wall is less than the second pressure on the LAA wall. The anchors 525 have a first position in the first post-deployment shape 502 and a second position in the second post-deployment shape 504. In embodiments, in the second position the anchors 525 pierce the LAA wall deeper than they do when in the first position.

Tenth Embodiment

Figure 6A:
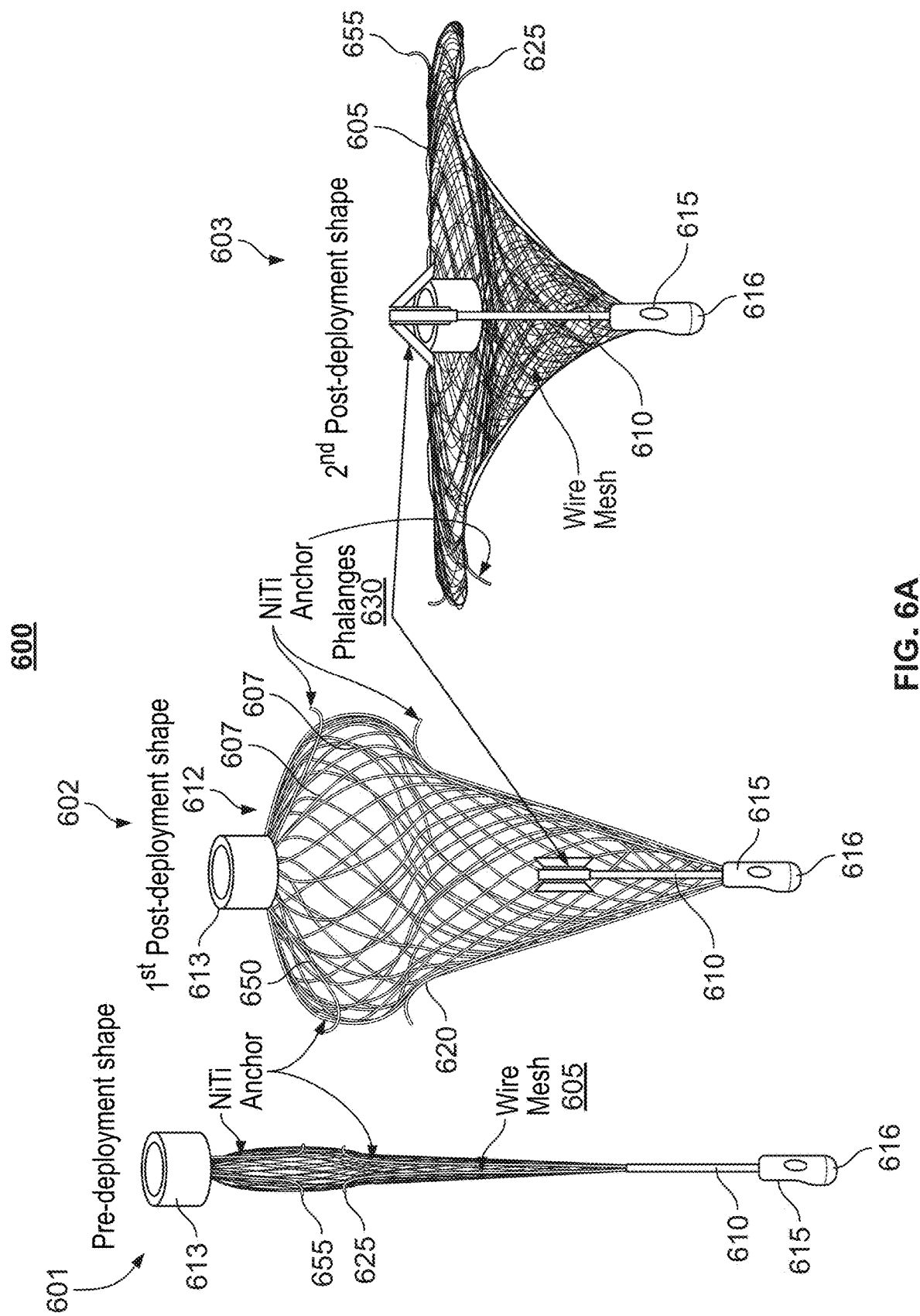
FIG. 6A shows pre-deployment, first post-deployment and second post-deployment shapes of another LAA occlusion device, in accordance with some embodiments of the present specification.
Figure 6B:
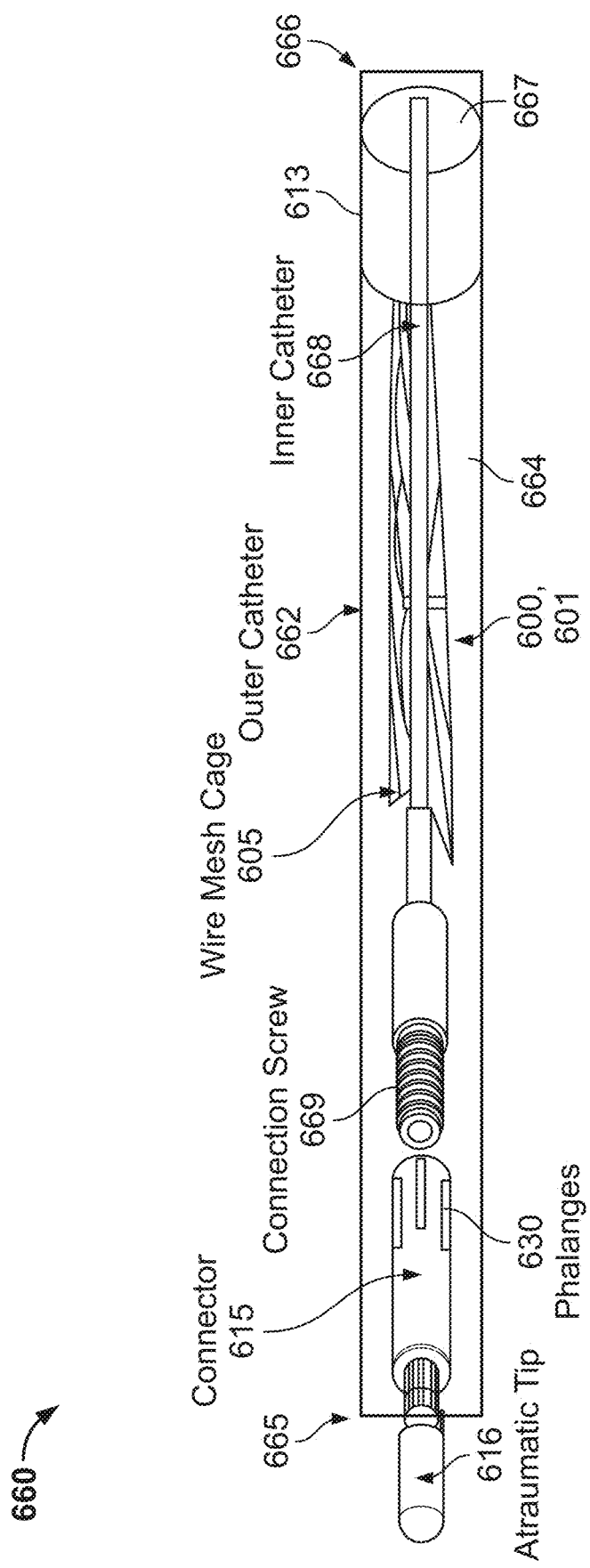
FIG. 6B shows a catheter system for deploying the LAA occlusion device of FIG. 6A into a left atrium of a patient's heart, in accordance with some embodiments of the present specification.
Figure 6C:
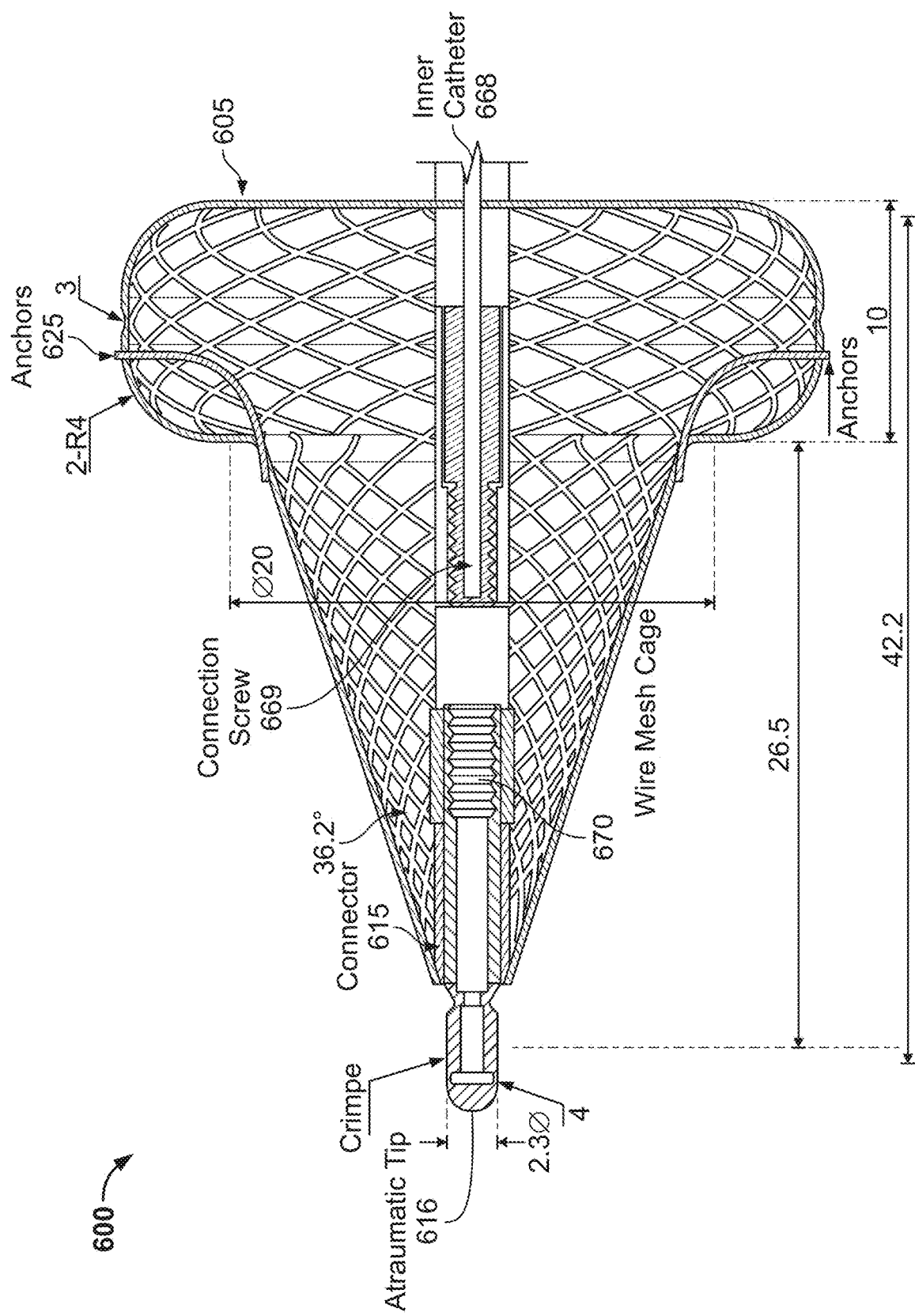
FIG. 6C shows a side cross-sectional view of the LAA occlusion device of FIG. 6A in the first post-deployment shape, in accordance with some embodiments of the present specification.
Figure 6E:
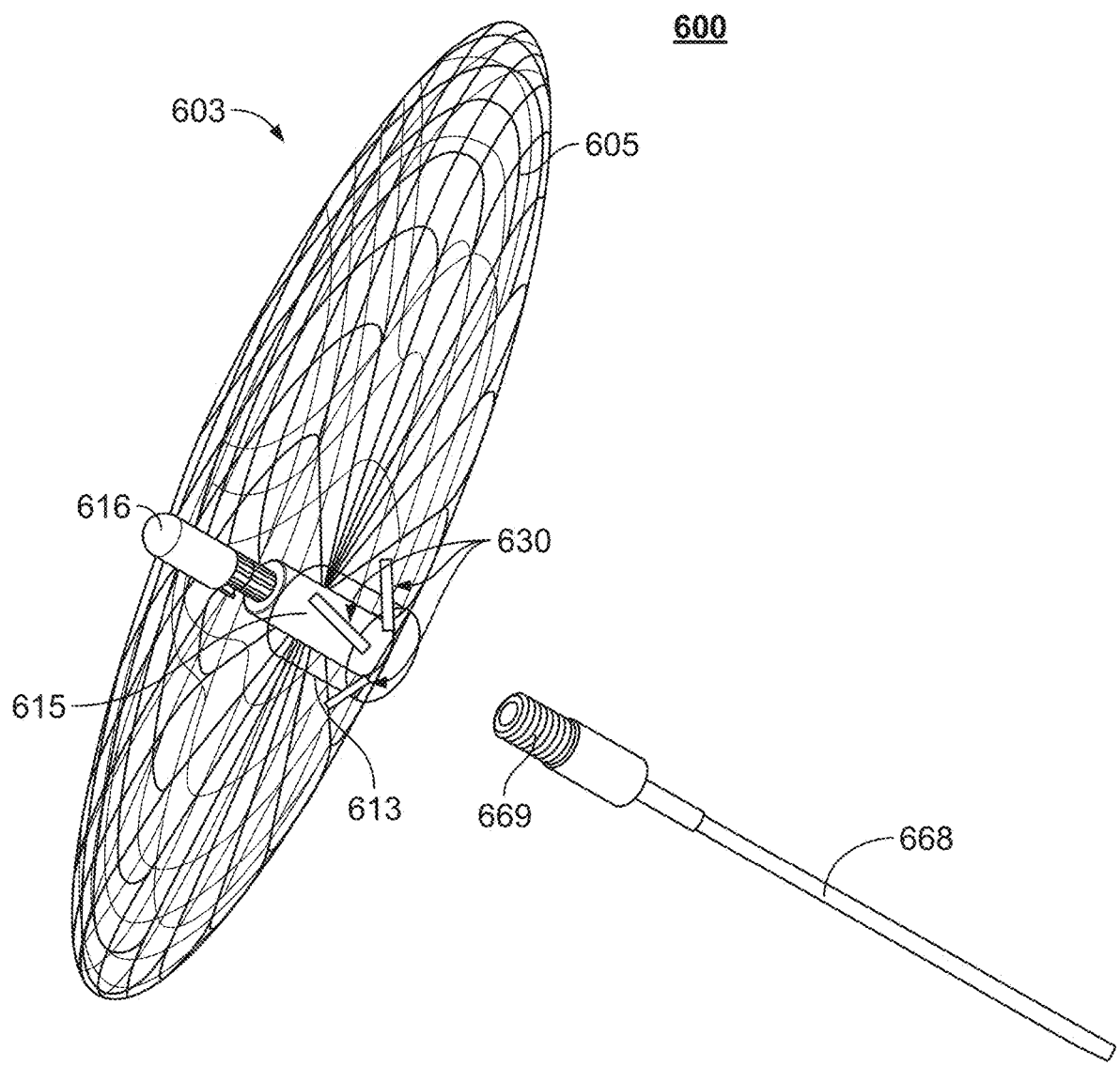
FIG. 6E shows a view of the LAA occlusion device of FIG. 6A in the second post-deployment shape, in accordance with some embodiments of the present specification.
Figure 6F:
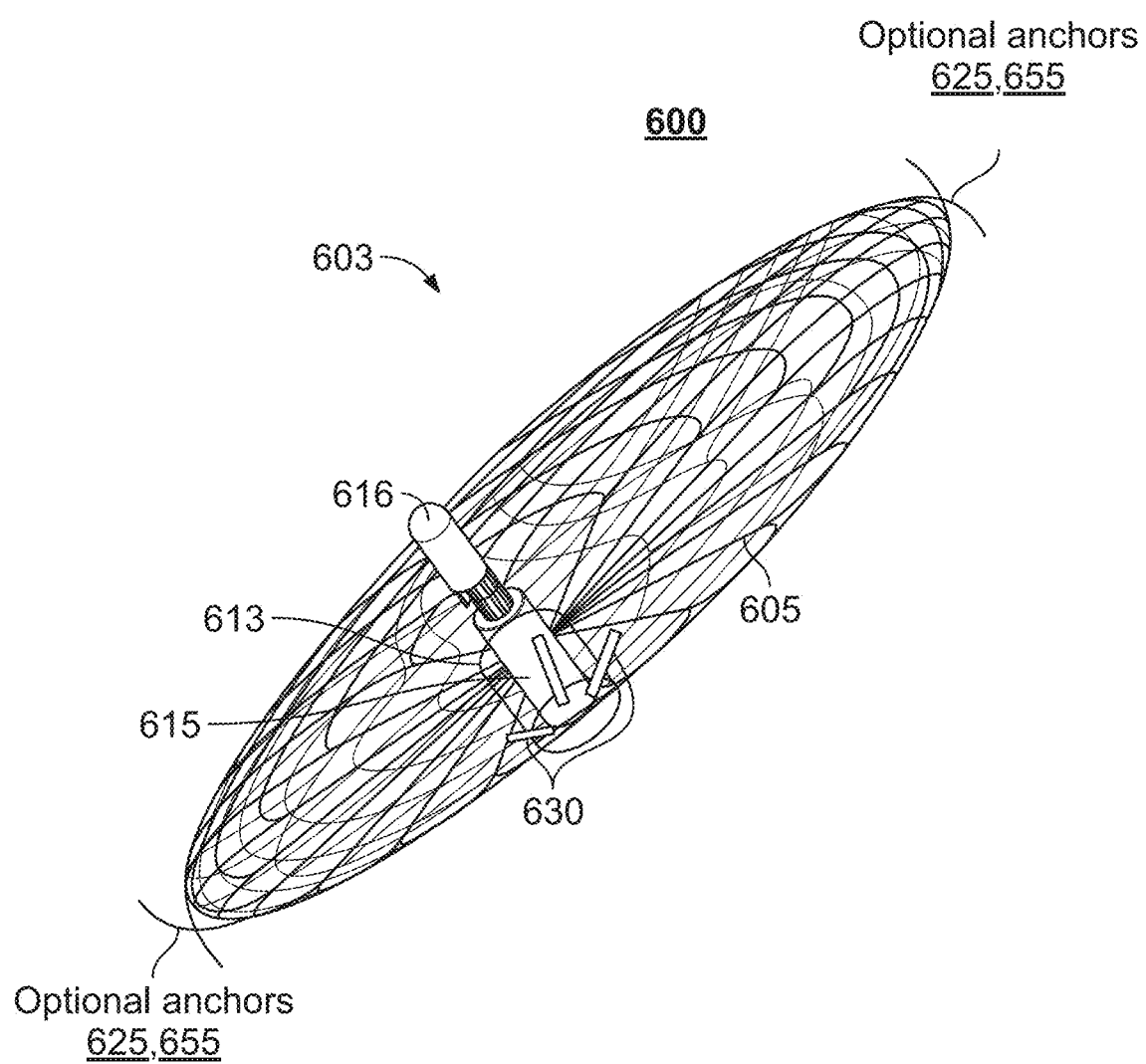
FIG. 6F shows another view of the LAA occlusion device of FIG. 6A in the second post-deployment shape with optional anchors, in accordance with some embodiments of the present specification.
Figure 6G:
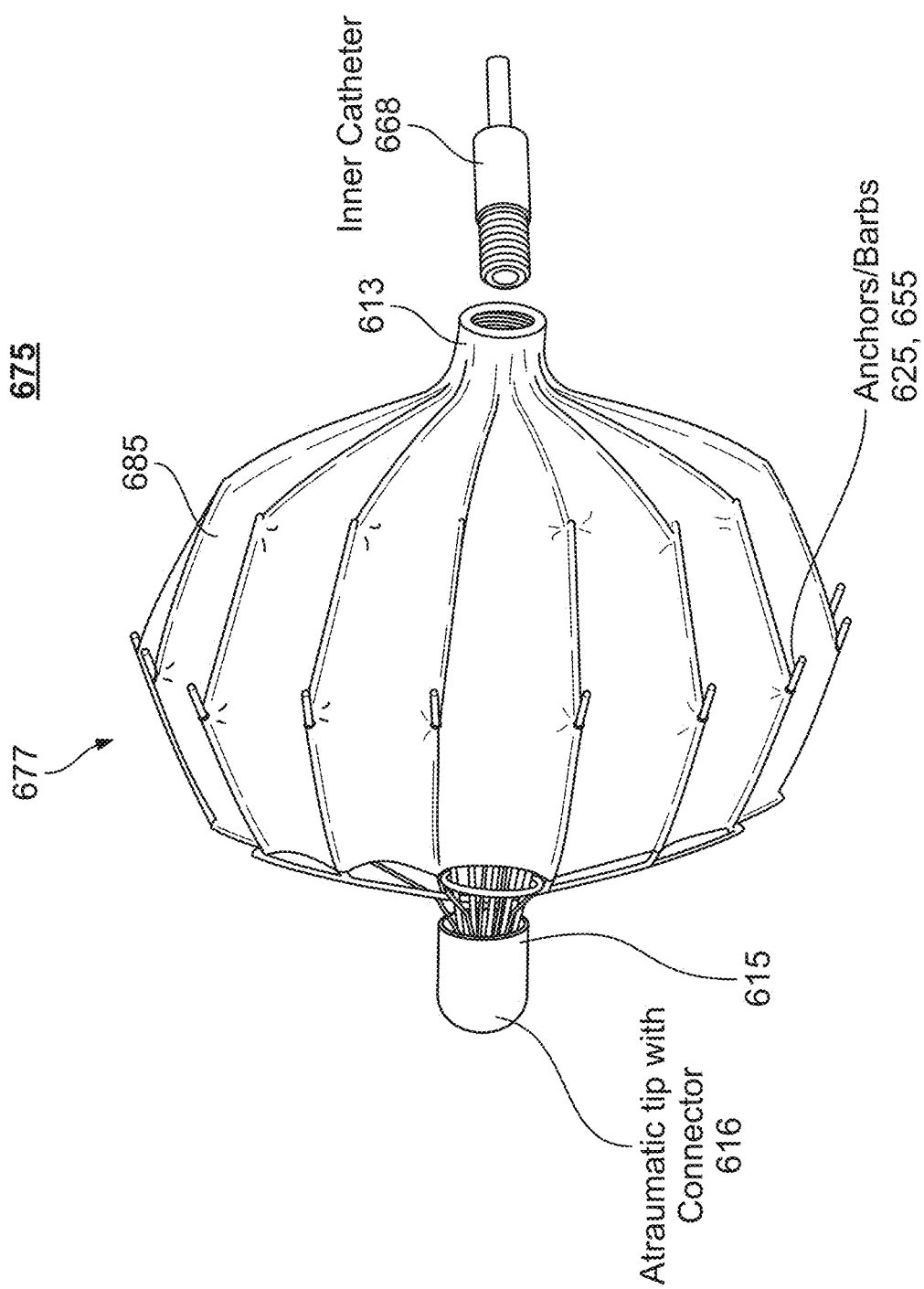
FIG. 6G shows a side view of another LAA occlusion device in a first post-deployment shape, in accordance with some embodiments of the present specification.
Figure 6I:
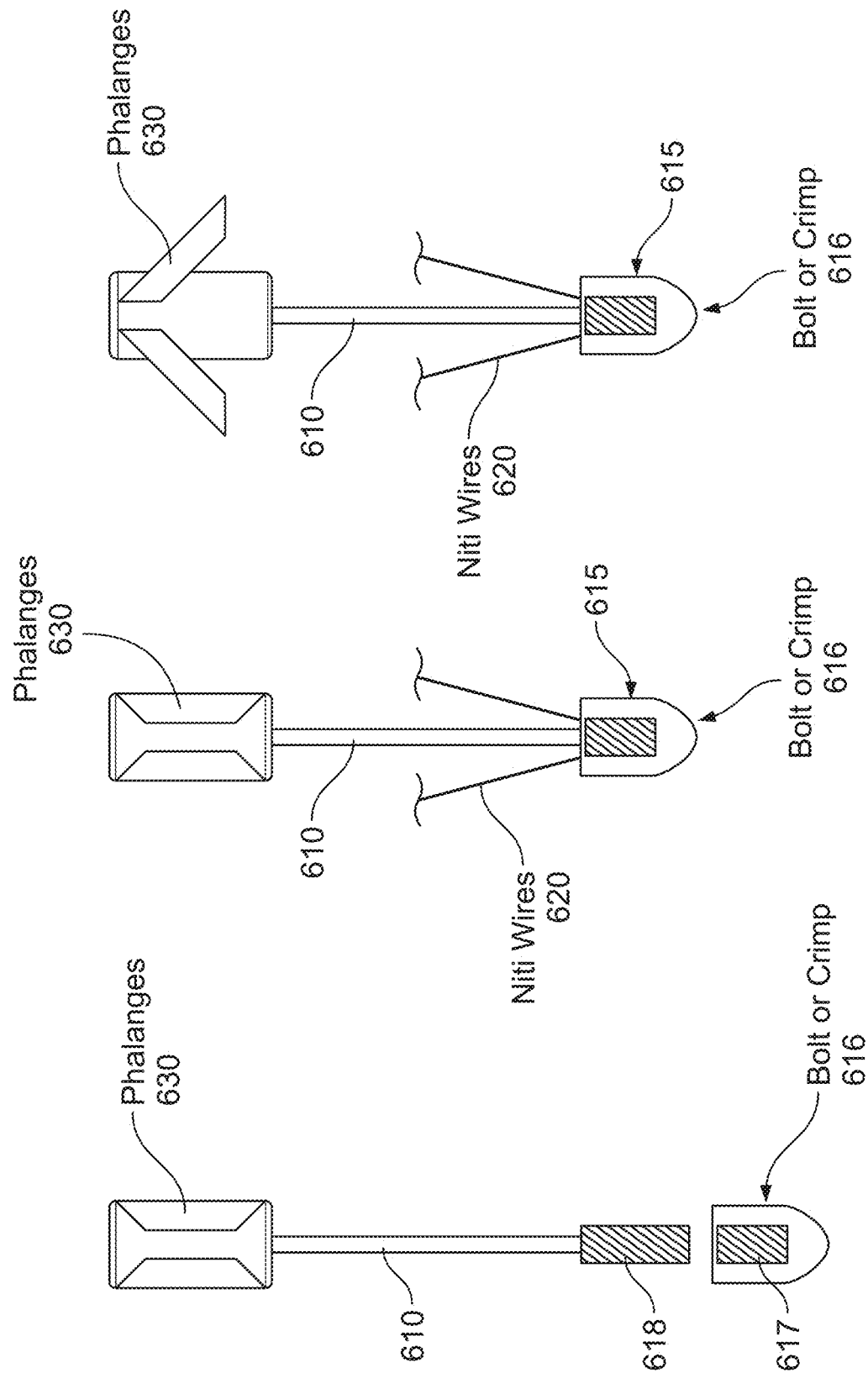
FIG. 6I shows different views of a central spine of the LAA occlusion device of FIG. 6A, in accordance with some embodiments of the present specification.

FIG. 6A shows pre-deployment, first post-deployment and second post-deployment shapes 601, 602, 603 while FIG. 6I shows different views of a rigid central member or spine 610 of an LAA occlusion device 600, in accordance with some embodiments of the present specification. Referring now to FIGS. 6A and 6B simultaneously, the device 600 has a wire mesh 605 that assumes a shape of an umbrella when the device 600 is in the second post-deployment shape 603. In some embodiments, the wire mesh 605 is a cage, frame, or web woven using a plurality of wires 607. The proximal surface of the device 600 is covered by a tissue ingrowth membrane for endothelialization of the proximal surface. The ingrowth membrane is made of any biocompatible material known in the art. In one embodiment, the membrane could be covered with or made of extracellular matrix. Proximal ends of the plurality of wires 607 of the wire mesh 605 are coupled to a first connector 613 positioned at a center 612 of the proximal surface of wire mesh 605 while distal ends of the plurality of wires 607 of the wire mesh 605 are coupled to a second connector 615. The second connector 615 is positioned at a distal end of the spine 610. A distal end of the second connector 615 comprises an atraumatic tip 616. In some embodiments, the tip 616 includes a substantially cylindrical bolt or crimp. A proximal end of the spine 610 has one or more phalanges 630 that have a first position (non-expanded) in the first post-deployment shape 602 and a second position (expanded) in the second post-deployment shape 603 of the device 600. In the first position or configuration, the plurality of phalanges is flush with the spine. In the second position or configuration, the plurality of phalanges extends outwardly from the spine. The $2^{nd}$ connector 615 is reversible connected to the inner pusher catheter 668 of FIG. 6B for deployment and retrieval of the device 600 and also for deployment of the phalanges 630. In various embodiments, the phalanges 630 are spring-loaded or magnetically actuated to enable deployment of the phalanges 630 as the LAA occlusion device 600 changes from the first post-deployment shape 602 to the second post-deployment shape 603. In various embodiments, the spine 610 and phalanges 630 are composed of a biocompatible material, such as stainless steel, titanium, or polyether ether ketone (PEEK).

Proximal ends of a first plurality of struts 620 of the wire mesh 605 are connected, coupled or attached to a first plurality of points along a perimeter of first connector 613 while distal ends of the first plurality of struts 620 are coupled to the second connector 615. Portions of the proximal tips of the first plurality of struts 620 extend beyond their respective points of attachment to form a first plurality of anchors 625 (also shown in FIG. 6C). In some embodiments, the proximal tips forming the first plurality of anchors 625 are angled or bent with respect to a substantially horizontal plane.

Proximal ends of a second plurality of struts 650 are connected, coupled or attached to a second plurality of points along a perimeter of the tissue ingrowth member 605 while distal ends of the second plurality of struts 650 are coupled to the second connector 615. Portions of the proximal tips of the second plurality of struts 650 extend beyond their respective points of attachment to form a second plurality of anchors 655. In some embodiments, the proximal tips forming the second plurality of anchors 655 are angled or bent with respect to a substantially horizontal plane. In some embodiments, the first plurality of points coincide with the second plurality of points of attachment. In alternate embodiments, the first plurality of points do not coincide with the second plurality of points of attachment.

In some embodiments, the plurality of wires 607 along with the first and second plurality of struts 620, 650 are of a shape memory material such as, for example, Nitinol. In some embodiments, the first and/or second plurality of anchors 625, 655 are optional.

As shown in FIG. 6I, the distal end of the second connector 615 comprises the atraumatic tip 616 of a substantially cylindrical bolt or crimp. An internal channel of the tip 616 includes a plurality of threads 617 that enable the tip 616 to thread over a plurality of threads 618 formed on an outer diameter of the distal end of the spine 610. The tip 616 enables fastening of the distal ends of the first plurality of struts 620.

As the device 600 changes shape from its pre-deployment shape 601 to its first and second post-deployment shapes 602, 603, the rigid spine 610 extends through the first connector 613 and the phalanges 630 engage with the first connector 613 to maintain the device 600 in its second post-deployment position.

In embodiments, the device 600 is configured into a pre-deployment shape 601 wherein the device 600 is compressed and positioned within a catheter, such as the catheter 660 of FIG. 6B. The device 600 assumes a first post-deployment shape 602 such that the device 600 is partially expanded upon being released from the catheter. Finally, the device 600 transitions to a second post-deployment shape 603 wherein the device 600 is fully expanded.

FIG. 6B shows a catheter system 660 for deploying the LAA occlusion device 600 into a left atrium of a patient's heart, in accordance with some embodiments of the present specification. The catheter system 660 includes an outer catheter 662 comprising a longitudinal cylindrical shaft having a central channel or lumen 664. As shown in FIG. 6B, the LAA occlusion device 600 is compressed to be in the pre-deployment shape 601 and positioned within the lumen 664 such that the atraumatic tip 616 and the second connector 615 lie at a distal end 665 while the tissue ingrowth member 605 and the first connector 613 lie towards a proximal end 666 of the outer catheter 662. In embodiments, the first connector 613 has a central channel or lumen 667 to enable an inner catheter 668 to be inserted axially through the channel 667 and engage with the second connector 615.

Referring now to FIGS. 6B, 6C and 6D, a distal end of the inner catheter 668 has a plurality of screw threads 669 that engage or lock with a corresponding plurality of threads 670 formed on an internal surface of a proximal end of the second connector 615. The proximal end of the second connector 615 includes the phalanges 630. Once engaged or locked, the inner catheter 668 is used to push the compressed device 600 through the distal end 665 proximate a LAA wall.

As shown in FIG. 6D, once released from the outer catheter 662, the device 600 assumes the first post-deployment shape 602. The inner catheter 668 is now pulled proximally thereby pulling the second connector 615 along so that the second connector 615 lies within the channel or lumen 667 of the first connector 613 and the expanded phalanges 630 protrude outside the channel 667 and engage a proximal end of the first connector 613. The phalanges 630 could be spring loaded and can be mechanically compressed and expanded. In one embodiment magnetic actuation is used to expand and compress the phalanges. As shown in FIG. 6E, as the second connector 615 is pulled toward the first connector 613, the device 600 assumes the second post-deployment shape 603 while the expanded phalanges 630, positioned at the proximal end of the first connector 613, maintain the device 600 in its second post-deployment shape 603. Once the device has been modulated to be in the second post-deployment shape 603, the inner catheter 668 is disengaged from the second connector 615, releasing the catheter from the device and deploying it in the LAA in its final, $2^{nd}$ post-deployment, position.

In some embodiments, the second post-deployment shape 603 has at least one dimension that is greater than the first post-deployment shape 602. In some embodiments, the second post-deployment shape 603 has at least one dimension that is lesser than the first post-deployment shape 602. In the first post-deployment shape 602 the device 600 exerts a first pressure on the LAA wall while in the second post-deployment shape 603 the device 600 exerts a second pressure on the LAA wall. In some embodiments, the first pressure on the LAA wall is less than the second pressure on the LAA wall. The first and second plurality of anchors 625, 655 have a first position in the first post-deployment shape 602 and a second position in the second post-deployment shape 603. FIG. 6C shows the first plurality of anchors 625 in the first position while FIG. 6F shows the first and second plurality of anchors 625, 655 in the second position. In embodiments, in the second position the first and second plurality of anchors 625, 655 pierce the LAA wall deeper than they do when in the first position. In other words, in the second position the first and second plurality of anchors 625, 655 protrude more than in the first position so as to engage the LAA wall more in the second post-deployment shape 603 than in the first post-deployment shape 602.

Eleventh Embodiment

FIGS. 6G and 6H show first post-deployment and second post-deployment shapes 677, 679 of another LAA occlusion device 675, in accordance with embodiments of the present specification. The device 675 of FIGS. 6G and 6H is similar to that of FIGS. 6A through 6F and 6I, with the difference of the tissue ingrowth member 685 that assumes a substantially spherical shape in the device 675 of FIGS. 6G and 6H compared to the umbrella shaped member 605 in the device 600 of FIGS. 6A through 6F.

In embodiments, the catheter system 660 of FIG. 6B is used for deploying the LAA occlusion device 675 into a left atrium of a patient's heart proximate an LAA. Accordingly, the device 600 is replaced with the device 675, in compressed shape, within the catheter system 660 for deployment.

As shown in FIG. 6G, once released from the outer catheter 662, the device 675 assumes the first post-deployment shape 677 while the inner catheter 668 is still engaged or locked with the second connector 615. The inner catheter 668 is subsequently pulled proximally thereby also pulling the second connector 615 along so that the second connector 615 lies within the channel or lumen 667 of the first connector 613 and the expanded phalanges 630 protrude outside the channel 667 and engage a proximal end of the first connector 613. As shown in FIG. 6H, as the second connector 615 is pulled towards the first connector 613, the device 675 assumes the second post-deployment shape 679 while the expanded phalanges 630, engaged with the proximal end of the first connector 613, maintain the device 675 in its second post-deployment shape 679. Once the device 675 has been modulated to be in the second post-deployment shape 679, the inner catheter 668 is disengaged from the second connector 615. In all deployments, the outer catheter 662 maintain the position the LAA occlusion device (300, 400, 500, 600, 675) relative to the LAA while the inner catheter 668 is used to pull the distal $2^{nd}$ connector 615 through the proximal 1st connector 613 to deploy the phalanges 630 and secure the device in its $2^{nd}$ post-deployment position.

In some embodiments, the second post-deployment shape 679 has at least one dimension that is greater than the first post-deployment shape 677. In some embodiments, the second post-deployment shape 679 has at least one dimension that is lesser than the first post-deployment shape 677. In the first post-deployment shape 677 the device 675 exerts a first pressure on the LAA wall while in the second post-deployment shape 679 the device 675 exerts a second pressure on the LAA wall. In some embodiments, the first pressure on the LAA wall is less than the second pressure on the LAA wall. The first and second plurality of anchors 625, 655 have a first position in the first post-deployment shape 677 and a second position in the second post-deployment shape 679. In embodiments, in the second position the first and second plurality of anchors 625, 655 pierce the LAA wall deeper than they do when in the first position. In other words, in the second position the first and second plurality of anchors 625, 655 protrude more than in the first position so as to engage the LAA wall more in the second post-deployment shape 679 than in the first post-deployment shape 677.

FIG. 7 shows a catheter 705 for deploying an LAA occlusion device 700 into a left atrium of a patient's heart proximate an LAA, in accordance with some embodiments of the present specification. The catheter 705 comprises a longitudinal cylindrical outer catheter 710 having a central channel or lumen 715. As shown, the LAA occlusion device 700 is compressed to be in a pre-deployment shape and positioned within the lumen 715 proximate a distal end 720 of the catheter 705. In some embodiments, first, second and third handles 725a, 725b, 725c are included at a proximal end 722 of the catheter 705. While the first and second handles 725a, 725b enable a user to effectively hold and manipulate the outer catheter 710, the third handle 725c enables the user to push the device 700 out of the lumen 715, using a plunger or inner catheter 730, for release into the left atrium proximate an LAA.

In various embodiments, the device 700 is any of the LAA occlusion devices 300, 350, 400, 450, 500 and 600 of the present specification.

Figure 8:
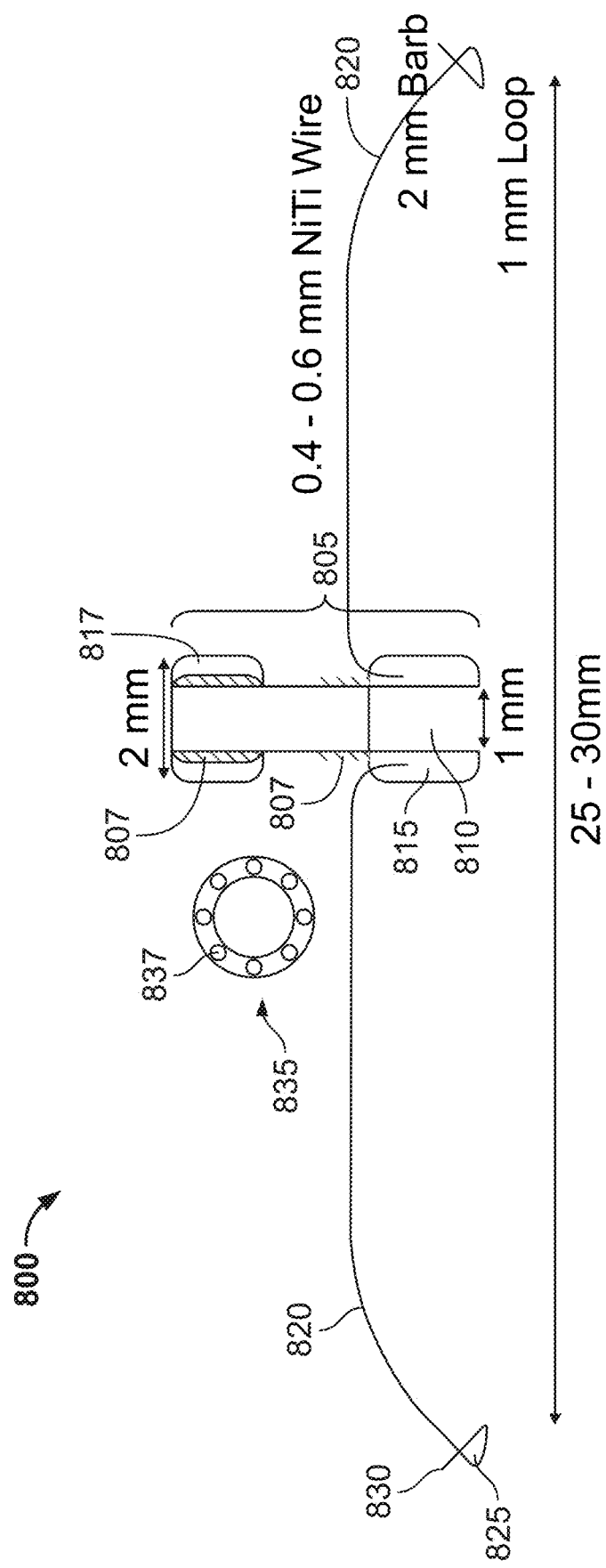
FIG. 8 is a cross-sectional view of a connector of an LAA occlusion device, in accordance with some embodiments of the present specification.

FIG. 8 is a cross-sectional view of a connector 800 of an LAA occlusion device, in accordance with some embodiments of the present specification. In various embodiments, the connector 800 is used in the LAA occlusion devices of the present specification. As shown, the connector 800 comprises a cylindrical element 805 having a plurality of threads 807 formed on an outer surface. The cylindrical element 805 has a central channel or lumen 810 to allow for passage of a rigid tine or spine in accordance with some embodiments of the present specification. In some embodiments, the channel or lumen 810 has an internal diameter of 1 mm. A proximal end of the cylindrical element 805 is secured by a bolt 815 while a distal end of the cylindrical element 805 has a nut or screw 817 that can be manipulated over the threads 807. In some embodiments, the bolt 815 and the nut/screw 817 have an outer diameter of 2 mm.

The bolt 815 clasps first ends of a plurality of struts 820. In some embodiments, each of the plurality of struts 820 is a Nitinol wire having a diameter ranging from 0.4 mm to 0.6 mm. In some embodiments, each of the plurality of struts 820 has a length ranging from 25 mm to 30 mm. Second ends of the plurality of struts 820 form a plurality of coupling loops 825 to connect to a plurality of corresponding points of attachment on a circumference or perimeter of a tissue ingrowth member of the LAA occlusion device. In some embodiments, each of the plurality of coupling loops 825 has a diameter of 1 mm. Portions of the second ends of the plurality of struts 820 extend beyond the plurality of corresponding points of attachment to a plurality of anchors 830. In some embodiments, each of the plurality of anchors 830 has a length of 2 mm. A cross-sectional, top-down view 835 of the connector 800 depicts a plurality of channels or chambers 837 within a wall of the connector 800. The channels 837 are configured to receive and hold the first ends of the plurality of struts 820 in place once the nut/screw 817 is tightened onto the bolt 815.

In all of the embodiments of the present specification, a plurality of electrically conductive elements may be configured to make contact with the LAA and LA wall. Electrical current can be passed through these electrically conductive elements to electrically stimulate or ablate cardiac tissue. For example, any one or more of the struts, connectors, extensions, barbs, tissue ingrowth members, connection points, or anchors may be configured to receive and deliver an electrical current to the cardiac tissue. Well known electrical parameters in the art can be used to stimulate or ablate cardiac tissue. The current can be monopolar or bipolar, radiofrequency current or current to induce electroporation in the LAA or LA tissue. The ablative effect can be used to ablate arrhythmogenic tissue proximate an LAA. The ablative effect can also be used to create fibrosis and help with anchoring of the LAA occlusion device. Radiofrequency (RF) energy and pulsed electric stimulation or electroporation can be used to ablate cardiac tissue through the device. The ablative energy is used to either ablate abnormal arrhythmogenic cardiac tissue or induce fibrosis to better anchor/secure the device.

FIG. 9 is a flowchart of a plurality of exemplary steps of a method of using an occlusion device to close an LAA, in accordance with some embodiments of the present specification. In various embodiments, the occlusion device is any of the LAA occlusion devices of the present specification.

At step 905, the device is positioned in a catheter in a pre-deployment shape wherein the device is in a compressed state. At step 910, using the catheter, the device is released proximate an LAA wall causing the device to partially expand into a first post-deployment shape and exert a first pressure on the LAA wall. At step 915, the device fully expands into a second post-deployment shape and exerts a second pressure on the LAA wall thereby closing the LAA. In some embodiments, the second pressure is greater than the first pressure.

In various embodiments, the second post-deployment shape has at least one dimension that is greater than the first post-deployment shape. In some embodiments, the second post-deployment shape has at least one dimension that is lesser than the first post-deployment shape.

In some embodiments, the first pressure is less than the second pressure on the LAA wall. In some embodiments, the second post-deployment shape has at least one dimension that is greater than the first post-deployment shape. In some embodiments, the second post-deployment shape has at least one dimension that is lesser than the first post-deployment shape.

In some embodiment, in the $1^{st}$ post-deployment position, the device can be repositioned in the LAAA or recaptured into the catheter for repositioning. In various embodiments, in the $2^{nd}$ post-deployment position, the device is locked in its final position in the LAA occluding the LAA.

The above examples are merely illustrative of the many applications of the system of the present invention. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention may be modified within the scope of the appended claims.

I claim:

1. A device adapted to treat a left atrial appendage (LAA) of a patient, the device comprising:
   a tissue ingrowth member;
   a connector;
   a central member having first and second ends, wherein the first end of the central member is positioned proximate a center of the tissue ingrowth member and the second end of the central member is coupled to the connector; and
   a plurality of struts having first and second ends, wherein the first ends of the plurality of struts are coupled to a plurality of corresponding points along a surface of the tissue ingrowth member, and wherein the second ends of the plurality of struts are coupled to the connector;
   wherein said device is configurable between a pre-deployment configuration, a first post-deployment configuration, and a second post-deployment configuration, further wherein, when in said first post-deployment configuration, the device has at least one first dimension and applies a first pressure against a cardiac wall and when in said second post-deployment configuration, said tissue ingrowth member has a substantially flat disc shape and the device has at least one second dimension and applies a second pressure against the cardiac wall, wherein said at least one second dimension is greater than said at least one first dimension and said second pressure is greater than said first pressure.

2. The device of claim 1, wherein the central member is rigid and includes a plurality of extensions along its length, and wherein the central member is configured to pass through the center of the tissue ingrowth member and the plurality of extensions is configured to engage and lock with the center of the tissue ingrowth member to lock the device in the second post-deployment configuration.

3. The device of claim 2, wherein the plurality of extensions comprises a plurality of barbs and wherein each of the plurality of barbs has a sharp edge tapering in one direction.

4. The device of claim 2, wherein said extensions are unidirectional.

5. The device of claim 1, wherein portions of the distal first ends of the plurality of struts extend beyond the surface of the tissue ingrowth member to form a plurality of anchors.

6. The device of claim 1, wherein the device is compressed into said pre-deployment configuration and configured to be positioned within, and delivered by, a catheter.

7. A method of using a device to close a left atrial appendage (LAA) in a patient, the method comprising:
   positioning the device in the LAA, wherein the device comprises a tissue ingrowth member, a connector, a central member having first and second ends with the first end of the central member positioned proximate a center of the tissue ingrowth member and the second end of the central member coupled to the connector, and a plurality of struts having first and second ends with the first ends of the plurality of struts coupled to a plurality of corresponding points along a circumference of the tissue ingrowth member and the second ends of the plurality of struts coupled to the connector, wherein the device is delivered in a pre-deployment configuration; and
   changing the device from the pre-deployment configuration to a first post-deployment configuration and then a second post-deployment configuration wherein, when in said first post-deployment configuration, the device has at least one first dimension and applies a first pressure against a cardiac wall and when in said second post-deployment configuration, said device has at least one second dimension and applies a second pressure against the cardiac wall, wherein said at least one second dimension is greater than said at least one first dimension and said second pressure is greater than said first pressure.

8. The method of claim 7, wherein the central member is rigid and includes a plurality of barbs along its length, and wherein the central member is configured to pass through said center of the tissue ingrowth member and said plurality of barbs is configured to engage and lock with said center of the tissue ingrowth member to lock said device in said second post-deployment configuration.

9. The method of claim 8, wherein said barbs are unidirectional.

* * * * *